United States Patent
Cheng et al.

(10) Patent No.: US 9,375,486 B2
(45) Date of Patent: Jun. 28, 2016

(54) OLIGOMER-CONTAINING BENZAMIDE-BASED COMPOUNDS

(71) Applicant: Nektar Therapeutics, San Francisco, CA (US)

(72) Inventors: Lin Cheng, Sunnyvale, CA (US); Jennifer Riggs-Sauthier, San Francisco, CA (US); Neel K. Anand, San Mateo, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 14/428,816

(22) PCT Filed: Sep. 17, 2013

(86) PCT No.: PCT/US2013/060179
§ 371 (c)(1),
(2) Date: Mar. 17, 2015

(87) PCT Pub. No.: WO2014/043707
PCT Pub. Date: Mar. 20, 2014

(65) Prior Publication Data
US 2015/0250894 A1    Sep. 10, 2015

Related U.S. Application Data

(60) Provisional application No. 61/702,088, filed on Sep. 17, 2012.

(51) Int. Cl.
| | |
|---|---|
| *C07C 231/12* | (2006.01) |
| *C07C 237/44* | (2006.01) |
| *A61K 47/48* | (2006.01) |
| *A61K 31/166* | (2006.01) |

(52) U.S. Cl.
CPC ......... *A61K 47/48215* (2013.01); *A61K 31/166* (2013.01); *C07C 231/12* (2013.01); *C07C 237/44* (2013.01)

(58) Field of Classification Search
None
See application file for complete search history.

(56) References Cited

U.S. PATENT DOCUMENTS

| | | |
|---|---|---|
| 3,177,252 A | 4/1965 | Thominet |
| 4,250,109 A | 2/1981 | Uchikuga et al. |
| 4,250,110 A | 2/1981 | Nishikido et al. |
| 4,810,646 A | 3/1989 | Jamas et al. |
| 4,992,540 A | 2/1991 | Jamas et al. |
| 5,028,703 A | 7/1991 | Jamas et al. |
| 5,227,397 A | 7/1993 | Saccomano et al. |
| 5,607,677 A | 3/1997 | Jamas et al. |
| 5,672,662 A | 9/1997 | Harris et al. |
| 5,741,495 A | 4/1998 | Jamas et al. |
| 2005/0136031 A1 | 6/2005 | Bentley et al. |
| 2005/0281781 A1 | 12/2005 | Ostroff |
| 2007/0015734 A1 | 1/2007 | McElroy et al. |
| 2008/0044438 A1 | 2/2008 | Ostroff et al. |

FOREIGN PATENT DOCUMENTS

| | | |
|---|---|---|
| GB | 1 500 105 | 2/1978 |
| WO | WO 02/098949 A1 | 12/2002 |
| WO | WO 2005/112943 A1 | 12/2005 |
| WO | WO 2012/100865 A1 | 8/2012 |

OTHER PUBLICATIONS

Chen, et al., "Synthesis and Properties of ABA Amphiphiles", J. Org. Chem., vol. 64, pp. 6870-6873, (1999).
Ertl, et al., "Fast Calculation of Molecular Polar Surface Area as a Sum of Fragment-Based Contributions and Its Application to the Prediction of Drug Transport", J. Med. Chem., vol. 43, pp. 3714-3717, (2000).
Gale, et al., "GR113808: a novel, selective antagonist with high affinity at the 5-HT$_4$ receptor", Br. J. Pharmacol. vol. 111, pp. 332-338, (1994).
Jasys, et al., "Isolation, Structure Elucidation, and Synthesis of Novel Hydroxylamine-Containing Polyamines from the Venom of the *Agelenopsis aperta* Spider", J. Am. Chem. Soc., vol. 112, pp. 6696-6704, (1990).
Kelder, et al., "Polar Molecular Surface as a Dominating Determinant for Oral Absorption and Brain Penetration of Drugs", Pharmaceutical Research, vol. 16, No. 10, pp. 1514-1519, (1999).
Mrksich, et al., "Biospecific-Adsorption of Carbonic Anhydrase to Self-Assembled Monolayers of Alkanethiolates That Present Benzenesulfonamide Groups on Gold", J. Am. Chem. Soc., vol. 117, pp. 12009-12010, (1995).
PCT International Search Report and Written Opinion corresponding to PCT Application No. PCT/US2013/060179 date of mailing Dec. 13, 2013.
PCT International Preliminary Report on Patentability corresponding to PCT Application No. PCT/US2013/060179 date of mailing Mar. 26, 2015.
ENZON Pharmaceuticals, Macromolecular Engineering Technologies, 16 pages, (2004).
NEKTAR™—Transforming Therapeutics, Nektar Molecule Engineering: Polyethylene Glycol and Derivatives for Advanced PEGylation, 24 pages, Catalog—2003, (Jul. 2003).
NEKTAR™—Transforming Therapeutics, Nektar Advanced PEGylation: Polyethylene Glycol and Derivatives for Advanced PEGylation, 27 pages, Catalog—2004, (Jul. 2004).
NEKTAR™—Transforming Therapeutics, Nektar Advanced PEGylation: Polyethylene Glycol and Derivatives for Advanced PEGylation, 33 pages, (Catalog 2005-2006).

(Continued)

*Primary Examiner* — Sudhakar Katakam
*Assistant Examiner* — Jennifer C Sawyer

(57) ABSTRACT

The invention relates to (among other things) oligomer-containing benzamide-based compounds. A compound of the invention exhibits one or more advantages over corresponding compounds lacking the oligomer.

12 Claims, 5 Drawing Sheets

(56) References Cited

OTHER PUBLICATIONS

NOF Corporation, PEG Derivatives, Phospholipid and Drug Delivery Materials for Pharmaceuticals, 46 pages, Catalogue 2003-1$^{st}$, (Jan. 2003).

NOF Corporation, PEG Derivatives, Phospholipid and Drug Delivery Materials for Pharmaceuticals, 27 pages, Catalogue 2003-2$^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

POLYPURE Products, PEG amines; PEG acids and amino acids; PEG thiols and disulfides; BIOTINS, 5 pages, (Apr. 2004).

POLYPURE Products, PEG amines; PEG acids and amino acids; PEG thiols and disulfides; BIOTINS, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

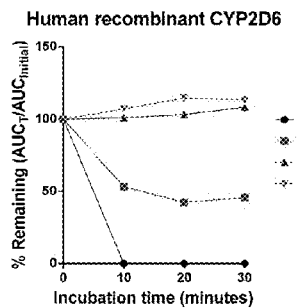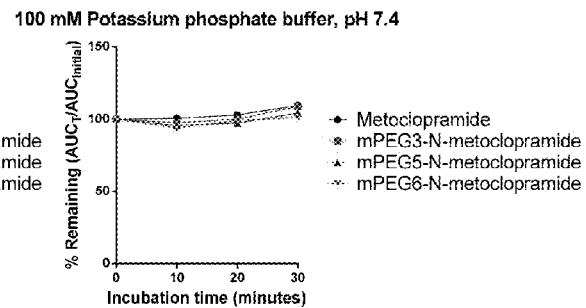
FIG. 5A          FIG. 5B
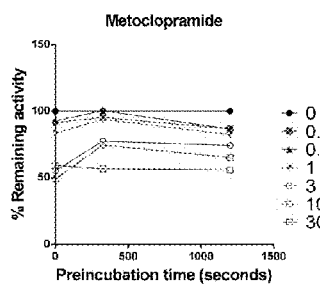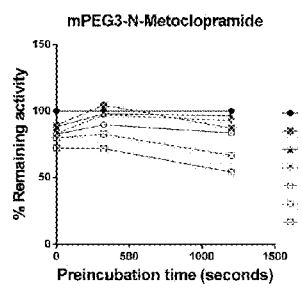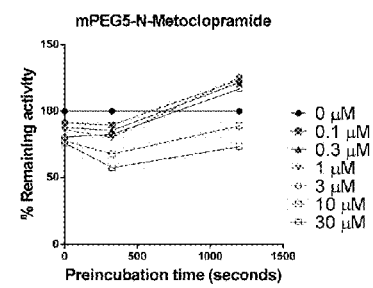
FIG. 6A          FIG. 6B          FIG. 6C
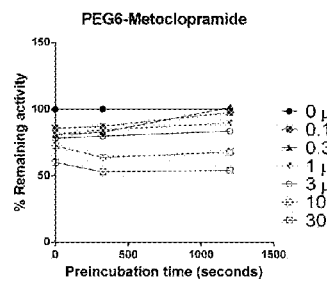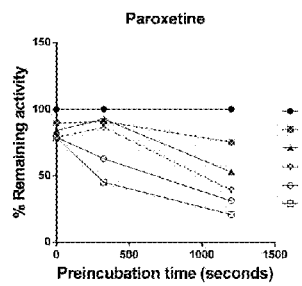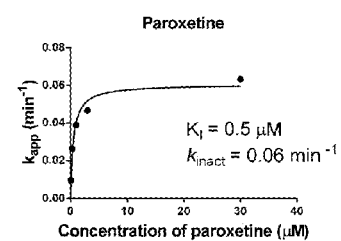
FIG. 6D          FIG. 6E          FIG. 6F

OLIGOMER-CONTAINING BENZAMIDE-BASED COMPOUNDS

CROSS REFERENCE TO RELATED APPLICATIONS

This application is a 35 U.S.C. §371 application of International Application No. PCT/US2013/060179, filed Sep. 17, 2013, designating the United States, which claims the benefit of priority under 35 U.S.C. §119(e) to U.S. Provisional Patent Application Ser. No. 61/702,088, filed on Sep. 17, 2012, the disclosures of which are incorporated herein by reference in their entireties.

FIELD OF THE INVENTION

This invention comprises (among other things) chemically modified benzamide-based compounds that possess certain advantages over benzamide-based compounds lacking the chemical modification. The chemically modified benzamide-based compounds described herein relate to and/or have application(s) in (among others) the fields of drug discovery, pharmacotherapy, physiology, organic chemistry and polymer chemistry.

BACKGROUND OF THE INVENTION

Chemical compounds based on a benzamide-based core exhibit a remarkable range of pharmacological actions in mammals.

benzamide

For example, N-(2-diethylaminoethyl)-2-methoxy-4-amino-5-chlorobenzamide (metoclopramide) is used in the treatment of patients suffering from gastroparesis. In addition, N-(2-diethyleaminoethyl)-4-amino-benzamide is used in the treatment of patients requiring class IA antiarrhythmic pharmacotherapy. Thus, these and other agents having a benzamide-based structure possess unique, and often beneficial, pharmacological properties.

The promise of these agents, however, has yet to be fully realized. For example, long term or high-dose use of metoclopramide increases the risk of tardive dyskinesia.

Thus, although benzamide-based compounds possess unique pharmacological properties, the ability to safely and efficaciously utilize these drugs has been limited.

Therefore, pharmacotherapy with benzamide-based compounds, such as metoclopramide, could be improved if new compounds could be provided that retained some degree of the pharmacology of this class of drugs, yet possessed different chemical structures, thereby resulting in different pharmacokinetic and/or pharmacodynamic profiles. As a consequence, there is an unmet need for developing novel benzamide-based compounds.

The present invention seeks to address these and other needs in the art.

SUMMARY OF THE INVENTION

In one or more embodiments of the invention, a compound is provided, the compound comprising a residue of a benzamide-based compound covalently attached via a stable or releasable linkage to a water-soluble, non-peptidic oligomer.

The "residue" of a benzamide-based compound is a compound having a structure of a therapeutically active benzamide-based compound that is altered by the presence of one or more bonds, which bonds serve to attach (either directly or indirectly) one or more water-soluble, non-peptidic oligomers.

Exemplary compounds of the invention include those having the following structure:

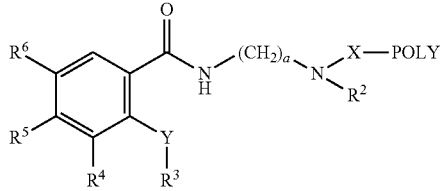

(Formula I-Ca)

wherein:
$R^2$ is lower alkyl (e.g., ethyl);
(a) is an integer in the range of from 1 to 4 inclusive (e.g., 2);
Y is either O (oxygen) or S;
$R^3$ is lower alkyl (e.g., methyl);
$R^4$ is selected from the group consisting of hydrogen, halo (e.g., chloro, bromo and iodo), lower alkoxy, amino, and lower alkylamino (e.g., hydrogen);
$R^5$ is selected from the group consisting of hydrogen, halo (e.g., chloro, bromo and iodo), lower alkoxy, amino, and lower alkylamino (e.g., amino);
$R^6$ is selected from the group consisting of hydrogen, halo (e.g., chloro, bromo and iodo), lower alkoxy, amino, and lower alkylamino (e.g., chloro);
X is a spacer moiety; and
POLY is a water-soluble, non-peptidic oligomer,
and pharmaceutically acceptable salts thereof.

Further exemplary compounds of the invention include those having the following structure:

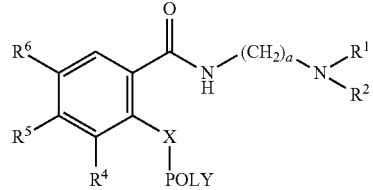

(Formula I-Cb)

wherein:
$R^1$ is lower alkyl (e.g., ethyl);
$R^2$ is lower alkyl (e.g., ethyl);
(a) is an integer in the range of from 1 to 4 inclusive (e.g., 2);
$R^4$ is selected from the group consisting of hydrogen, halo (e.g., chloro, bromo and iodo), lower alkoxy, amino, and lower alkylamino (e.g., hydrogen);
$R^5$ is selected from the group consisting of hydrogen, halo (e.g., chloro, bromo and iodo), lower alkoxy, amino, and lower alkylamino (e.g., amino);
$R^6$ is selected from the group consisting of hydrogen, halo (e.g., chloro, bromo and iodo), lower alkoxy, amino, and lower alkylamino (e.g., chloro);

X is a spacer moiety; and
POLY is a water-soluble, non-peptidic oligomer,
and pharmaceutically acceptable salts thereof.

Further exemplary compounds of the invention include those having the following structure:

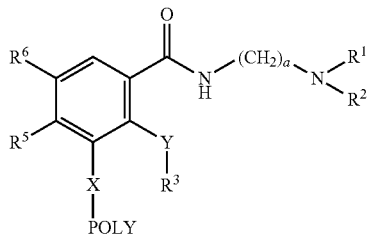

(Formula I-Cc)

wherein:
R¹ is lower alkyl (e.g., ethyl);
R² is lower alkyl (e.g., ethyl);
(a) is an integer in the range of from 1 to 4 inclusive (e.g., 2);
Y is either O (oxygen) or S;
R³ is lower alkyl (e.g., methyl);
R⁵ is selected from the group consisting of hydrogen, halo (e.g., chloro, bromo and iodo), lower alkoxy, amino, and lower alkylamino (e.g., amino);
R⁶ is selected from the group consisting of hydrogen, halo (e.g., chloro, bromo and iodo), lower alkoxy, amino, and lower alkylamino (e.g., chloro);
X is a spacer moiety; and
POLY is a water-soluble, non-peptidic oligomer,
and pharmaceutically acceptable salts thereof.

Still further exemplary compounds of the invention include those having the following structure:

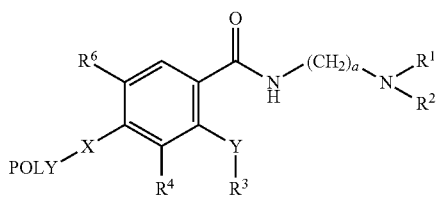

(Formula I-Cd)

wherein:
R¹ is lower alkyl (e.g., ethyl);
R² is lower alkyl (e.g., ethyl);
(a) is an integer in the range of from 1 to 4 inclusive (e.g., 2);
Y is either O (oxygen) or S;
R³ is lower alkyl (e.g., methyl);
R⁴ is selected from the group consisting of hydrogen, halo (e.g., chloro, bromo and iodo), lower alkoxy, amino, and lower alkylamino (e.g., hydrogen);
R⁶ is selected from the group consisting of hydrogen, halo (e.g., chloro, bromo and iodo), lower alkoxy, amino, and lower alkylamino (e.g., chloro);
X is a spacer moiety; and
POLY is a water-soluble, non-peptidic oligomer,
and pharmaceutically acceptable salts thereof.

Still further exemplary compounds of the invention include those having the following structure:

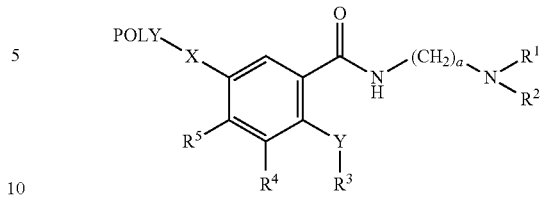

(Formula I-Ce)

wherein:
R¹ is lower alkyl (e.g., ethyl);
R² is lower alkyl (e.g., ethyl);
(a) is an integer in the range of from 1 to 4 inclusive (e.g., 2);
Y is either O (oxygen) or S;
R³ is lower alkyl (e.g., methyl);
R⁴ is selected from the group consisting of hydrogen, halo (e.g., chloro, bromo and iodo), lower alkoxy, amino, and lower alkylamino (e.g., hydrogen);
R⁵ is selected from the group consisting of hydrogen, halo (e.g., chloro, bromo and iodo), lower alkoxy, amino, and lower alkylamino (e.g., amine);
X is a spacer moiety; and
POLY is a water-soluble, non-peptidic oligomer,
and pharmaceutically acceptable salts thereof.

With respect to the benzamide-based compound, as used herein a benzamide-based compound has a structure encompassed by Formula I:

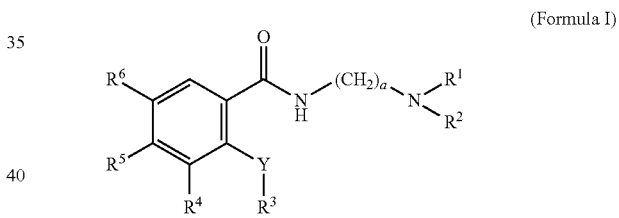

(Formula I)

wherein:
R¹ is lower alkyl (e.g., ethyl);
R² is lower alkyl (e.g., ethyl);
(a) is an integer in the range of from 1 to 4 inclusive (e.g., 2);
Y is either O (oxygen) or S;
R³ is lower alkyl (e.g., methyl);
R⁴ is selected from the group consisting of hydrogen, halo (e.g., chloro, bromo and iodo), lower alkoxy, amino, and lower alkylamino (e.g., hydrogen);
R⁵ is selected from the group consisting of hydrogen, halo (e.g., chloro, bromo and iodo), lower alkoxy, amino, and lower alkylamino (e.g., amine); and
R⁶ is selected from the group consisting of hydrogen, halo (e.g., chloro, bromo and iodo), lower alkoxy, amino, and lower alkylamino (e.g., chloro),
and pharmaceutically acceptable salts thereof.

Exemplary benzamide-based compound moieties for use in the current invention are selected from the group consisting of metoclopramide and procainamide.

In one or more embodiments of the invention, a composition is provided, the composition comprising a compound comprising a residue of benzamide-based compound covalently attached via a stable or releasable linkage to a water-soluble, non-peptidic oligomer, and optionally, a pharmaceutically acceptable excipient.

In one or more embodiments of the invention, a dosage form is provided, the dosage form comprising a compound comprising a residue of benzamide-based compound covalently attached via a stable or releasable linkage to a water-soluble, non-peptidic oligomer, wherein the compound is present in a dosage form.

In one or more embodiments of the invention, a method is provided, the method comprising covalently attaching a water-soluble, non-peptidic oligomer to a benzamide-based compound.

In one or more embodiments of the invention, a method is provided, the method comprising administering a compound to a mammal in need thereof, the compound comprising a residue of benzamide-based compound covalently attached via a stable or releasable linkage to a water-soluble, non-peptidic oligomer.

Additional embodiments of the present conjugates, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims.

BRIEF DESCRIPTION OF THE FIGURES

FIG. 5A is a plot of the results of a metabolic stability study of test articles in a human recombinant CYP2D6 enzyme, as carried out in the manner described Example 18.

FIG. 5B is a plot of the results of a chemical stability study of test articles in a 100 mM potassium phosphate buffer, pH 7.4 at 37° C. for up to thirty minutes.

FIGS. 6A through 6F are a series of plots representing the extent of inhibition of CYP2D6 by test articles at a series of concentrations, as carried out in the manner described Example 12.

DETAILED DESCRIPTION OF THE INVENTION

Figure 1:
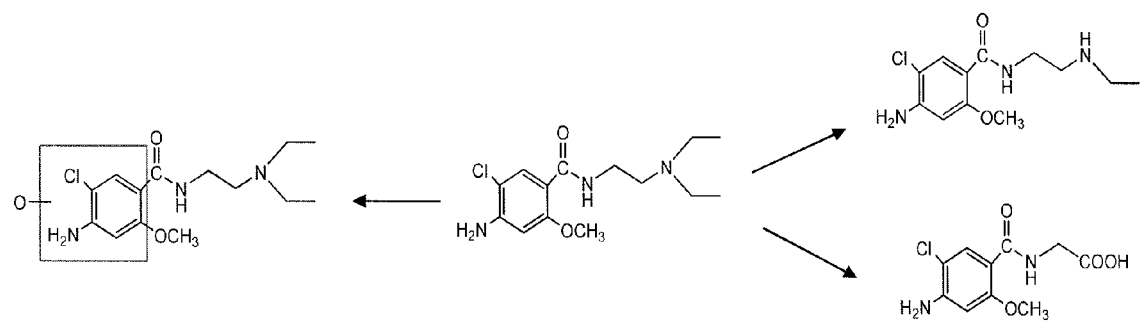
FIG. 1 is a schematic of the metabolic pathway of metoclopramide.

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with the present invention are homo-oligomers. The water-soluble, non-peptidic oligomer comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though, the oligomer may contain distinct end capping moieties or functional groups, e.g., for conjugation. PEG oligomers for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. As stated above, for the PEG oligomers, the variable (n) ranges from about 1 to 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

"Branched," in reference to the geometry or overall structure of an oligomer, refers to an oligomer having two or more polymer "arms" extending from a branch point.

"Forked," in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the therapeutic moiety. A composition comprised of monodisperse conjugates may, however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the therapeutic moiety. A composition comprised of bimodal conjugates may, however, include one or more nonconjugate substances such as solvents, reagents, excipients, and so forth.

A "benzamide-based compound" is broadly used herein to refer to an organic, inorganic, or organometallic compound having a molecular weight of less than about 1000 Daltons and having some degree of pharmacological activity (e.g., gastric motility). Assays known to those of ordinary skill in the art can be used to determine whether a given benzamide-based compound (as well as an oligomer-containing compound provided herein) has pharmacological activity (e.g., gastric motility).

A "biological membrane" is any membrane made of cells or tissues that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate," provides a measure of a compound's ability to cross a biological membrane, such as the blood-brain barrier ("BBB"). A variety of methods may be used to assess transport of a molecule across any given biological membrane. Methods to assess the biological membrane crossing rate associated with any given biological barrier (e.g., the blood-brain barrier, blood-cerebrospinal fluid barrier, the blood-placental barrier, the blood-milk barrier, the intestinal barrier, and so forth), are known, described herein and/or in the relevant literature, and/or may be determined by one of ordinary skill in the art.

A "reduced metabolism" refers to a measurable reduction in metabolism and/or to a measured reduction of the rate of metabolism of a water-soluble oligomer-small molecule drug conjugate as compared to the rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and may pass through the liver prior to reaching the systemic circulation. Because the liver is the primary site of drug metabolism or biotransformation, a substantial amount of drug may be metabolized before it ever reaches the systemic circulation. The degree of first pass metabolism, and thus, any reduction thereof, may be measured by a number of different approaches. For instance, animal blood samples may be collected at timed intervals and the plasma or serum analyzed by liquid chromatography/mass spectrometry for metabolite levels. Other techniques for measuring a "reduced rate of metabolism" associated with the first pass metabolism and other metabolic processes are known, described herein and/or in the relevant literature, and/or may be determined by one of ordinary skill in the art. Preferably, a compound of the invention may provide a reduced rate of metabolism (relative to a compound lacking a water-soluble, non-peptidic oligomers) satisfying at least one of the following values: at least about 30%; at least about 40%; at least about 50%; at least about 60%; at least about 70%; at least about 80%; and at least about 90%. A compound (such as a small molecule drug or conjugate thereof) that is "orally bioavailable" is one that preferably possesses a bioavailability when administered orally of greater than 25%, and preferably greater than 70%, where a compound's bioavailability is the fraction of administered drug that reaches the systemic circulation in unmetabolized form.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced. An "alkenyl" group is an alkyl of 2 to 20 carbon atoms with at least one carbon-carbon double bond.

The terms "substituted alkyl" or "substituted $C_q$, alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclic, amino, phenoxy, nitro, carboxy, acyl, cyano. The substituted alkyl groups may be substituted once, twice or three times with the same or with different substituents.

"Lower alkyl" refers to an alkyl group containing from 1 to 6 carbon atoms, and may be straight chain or branched, as exemplified by methyl, ethyl, propyl, i-propyl, n-butyl, i-butyl, t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$. "Lower alkoxy" is —O—R, wherein R is a $C_1$-$C_7$ alkyl.

"Pharmaceutically acceptable excipient" or "pharmaceutically acceptable carrier" refers to a component that may be included in the compositions of the invention causes no significant adverse toxicological effects to a patient.

The term "aryl" means an aromatic group having up to 14 carbon atoms. Aryl groups include phenyl, naphthyl, biphenyl, phenanthrenyl, naphthalenyl, and the like. "Substituted phenyl" and "substituted aryl" denote a phenyl group and aryl group, respectively, substituted with one, two, three, four or five (e.g., 1-2, 1-3 or 1-4 substituents) chosen from halo (e.g., F, Cl, Br, I), hydroxy, cyano, nitro, alkyl (e.g., $C_{1-6}$ alkyl), alkoxy (e.g., $C_{1-6}$ alkoxy), benzyloxy, carboxy, aryl, and so forth.

"Pharmacologically effective amount," "physiologically effective amount," and "therapeutically effective amount" are used interchangeably herein to mean the amount of the compound of the invention present in a composition that is needed to provide a desired level of the compound (or desired metabolite thereof) in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterodifunctional.

A basic reactant or an acidic reactant described herein include neutral, charged, and any corresponding salt forms thereof.

The term "patient," refers to a living organism suffering from or prone to a condition that can be prevented or treated by administration of a compound of the invention as described herein, and includes animals and humans (and other mammals).

"Optional" or "optionally" means that the subsequently described circumstance may but need not necessarily occur, so that the description includes instances where the circumstance occurs and instances where it does not.

As indicated above, the present invention is directed to (among other things) a compound comprising a residue of benzamide-based compound covalently attached via a stable or releasable linkage to a water-soluble, non-peptidic oligomer.

The residue of "benzamide-based compound" is a compound having a structure of a benzamide-based compound that is altered by the presence of one or more bonds, which bonds serve to attach (either directly or indirectly) one or more water-soluble, non-peptidic oligomers. Exemplary benzamide-based compound moieties have a structure encompassed by Formula I:

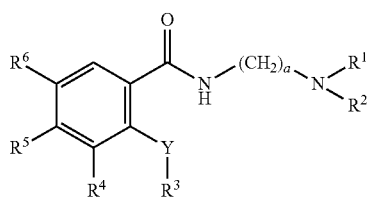

(Formula I)

wherein:

$R^1$ is lower alkyl (e.g., ethyl);

$R^2$ is lower alkyl (e.g., ethyl);

(a) is an integer in the range of from 1 to 4 inclusive (e.g., 2);

Y is either O (oxygen) or S;

$R^3$ is lower alkyl (e.g., methyl);

$R^4$ is selected from the group consisting of hydrogen, halo (e.g., chloro, bromo and iodo), lower alkoxy, amino, and lower alkylamino (e.g., hydrogen);

$R^5$ is selected from the group consisting of hydrogen, halo (e.g., chloro, bromo and iodo), lower alkoxy, amino, and lower alkylamino (e.g., amine); and $R^6$ is selected from the group consisting of hydrogen, halo (e.g., chloro, bromo and iodo), lower alkoxy, amino, and lower alkylamino (e.g., chloro), and pharmaceutically acceptable salts thereof.

In one or more embodiments of the invention, a compound is provided, the compound comprising a residue of a benzamide-based compound covalently attached via a stable or releasable linkage to a water-soluble, non-peptidic oligomer, wherein the benzamide-based compound (in a form in which the water-soluble, non-peptidic oligomer is not present) corresponds to a benzamide-based compound selected from the group consisting of metoclopramide and procainamide In some instances, a benzamide-based compound that is useful as a starting material or intermediate in synthesizing the compounds of the invention can be obtained from commercial sources. In addition, benzamide-based compound can be obtained through chemical synthesis. Synthetic approaches for preparing benzamide-based compounds are described in the literature and in, for example, U.S. Pat. No. 4,250,110. Each of these (and other) benzamide-based compounds can be covalently attached (either directly or through one or more atoms) to a water-soluble, non-peptidic oligomer following the techniques and approaches described herein.

Exemplary compounds of the invention include those having the following structure:

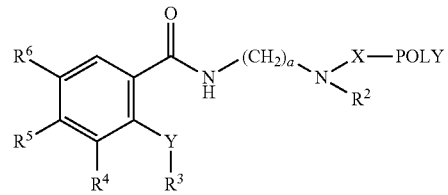

(Formula I-Ca)

wherein:

$R^2$ is lower alkyl (e.g., ethyl);

(a) is an integer in the range of from 1 to 4 inclusive (e.g., 2);

Y is either O (oxygen) or S;

$R^3$ is lower alkyl (e.g., methyl);

$R^4$ is selected from the group consisting of hydrogen, halo (e.g., chloro, bromo and iodo), lower alkoxy, amino, and lower alkylamino (e.g., hydrogen);

$R^5$ is selected from the group consisting of hydrogen, halo (e.g., chloro, bromo and iodo), lower alkoxy, amino, and lower alkylamino (e.g., amino);

$R^6$ is selected from the group consisting of hydrogen, halo (e.g., chloro, bromo and iodo), lower alkoxy, amino, and lower alkylamino (e.g., chloro);

X is a spacer moiety; and

POLY is a water-soluble, non-peptidic oligomer, and pharmaceutically acceptable salts thereof.

Further exemplary compounds of the invention include those having the following structure:

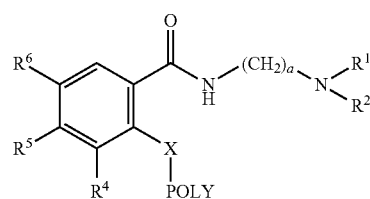

(Formula I-Cb)

wherein:

$R^1$ is lower alkyl (e.g., ethyl);

$R^2$ is lower alkyl (e.g., ethyl);

(a) is an integer in the range of from 1 to 4 inclusive (e.g., 2);

$R^4$ is selected from the group consisting of hydrogen, halo (e.g., chloro, bromo and iodo), lower alkoxy, amino, and lower alkylamino (e.g., hydrogen);

$R^5$ is selected from the group consisting of hydrogen, halo (e.g., chloro, bromo and iodo), lower alkoxy, amino, and lower alkylamino (e.g., amino);

$R^6$ is selected from the group consisting of hydrogen, halo (e.g., chloro, bromo and iodo), lower alkoxy, amino, and lower alkylamino (e.g., chloro);

X is a spacer moiety; and

POLY is a water-soluble, non-peptidic oligomer, and pharmaceutically acceptable salts thereof.

Further exemplary compounds of the invention include those having the following structure:

(Formula I-Cc)

wherein:
R¹ is lower alkyl (e.g., ethyl);
R² is lower alkyl (e.g., ethyl);
(a) is an integer in the range of from 1 to 4 inclusive (e.g., 2);
Y is either O (oxygen) or S;
R³ is lower alkyl (e.g., methyl);
R⁵ is selected from the group consisting of hydrogen, halo (e.g., chloro, bromo and iodo), lower alkoxy, amino, and lower alkylamino (e.g., amino);
R⁶ is selected from the group consisting of hydrogen, halo (e.g., chloro, bromo and iodo), lower alkoxy, amino, and lower alkylamino (e.g., chloro);
X is a spacer moiety; and
POLY is a water-soluble, non-peptidic oligomer,
and pharmaceutically acceptable salts thereof.

Still further exemplary compounds of the invention include those having the following structure:

(Formula I-Cd)

wherein:
R¹ is lower alkyl (e.g., ethyl);
R² is lower alkyl (e.g., ethyl);
(a) is an integer in the range of from 1 to 4 inclusive (e.g., 2);
Y is either O (oxygen) or S;
R³ is lower alkyl (e.g., methyl);
R⁴ is selected from the group consisting of hydrogen, halo (e.g., chloro, bromo and iodo), lower alkoxy, amino, and lower alkylamino (e.g., hydrogen);
R⁶ is selected from the group consisting of hydrogen, halo (e.g., chloro, bromo and iodo), lower alkoxy, amino, and lower alkylamino (e.g., chloro);
X is a spacer moiety; and
POLY is a water-soluble, non-peptidic oligomer,
and pharmaceutically acceptable salts thereof.

Still further exemplary compounds of the invention include those having the following structure:

(Formula I-Ce)

wherein:
R¹ is lower alkyl (e.g., ethyl);
R² is lower alkyl (e.g., ethyl);
(a) is an integer in the range of from 1 to 4 inclusive (e.g., 2);
Y is either O (oxygen) or S;
R³ is lower alkyl (e.g., methyl);
R⁴ is selected from the group consisting of hydrogen, halo (e.g., chloro, bromo and iodo), lower alkoxy, amino, and lower alkylamino (e.g., hydrogen);
R⁵ is selected from the group consisting of hydrogen, halo (e.g., chloro, bromo and iodo), lower alkoxy, amino, and lower alkylamino (e.g., amine);
X is a spacer moiety; and
POLY is a water-soluble, non-peptidic oligomer,
and pharmaceutically acceptable salts thereof.

Exemplary compounds of the invention include, for example, those selected from the group consisting of (wherein X is a spacer moiety and POLY is a water-soluble, non-peptidic oligomer);

(wherein n is an integer of from 1 to 30, inclusive);

(wherein n is an integer of from 1 to 30, inclusive);

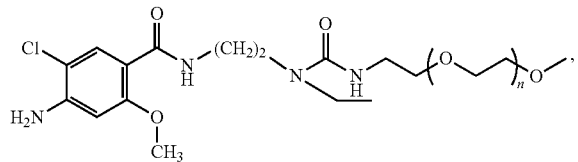

(wherein n is an integer of from 1 to 30, inclusive);

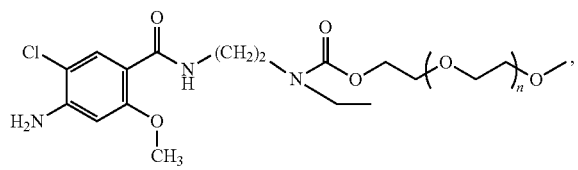

(wherein n is an integer of from 1 to 30, inclusive);

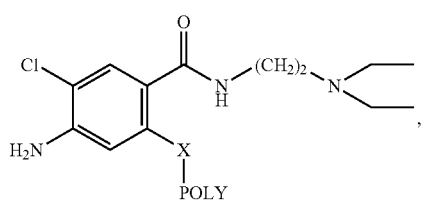

(wherein X is a spacer moiety and POLY is a water-soluble, non-peptidic oligomer);

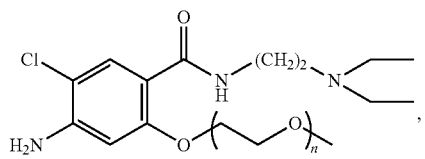

(wherein n is an integer of from 1 to 30, inclusive);

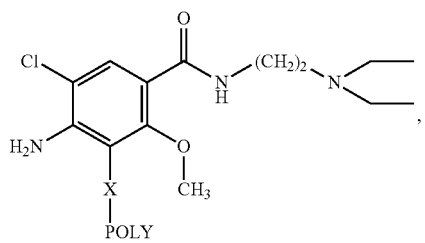

(wherein X is a spacer moiety and POLY is a water-soluble, non-peptidic oligomer);

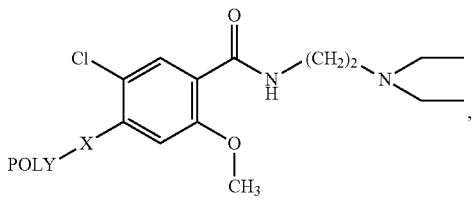

(wherein X is a spacer moiety and POLY is a water-soluble, non-peptidic oligomer);

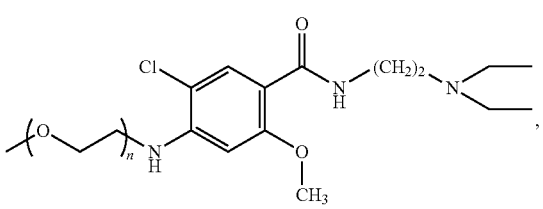

(wherein n is an integer of from 1 to 30, inclusive);

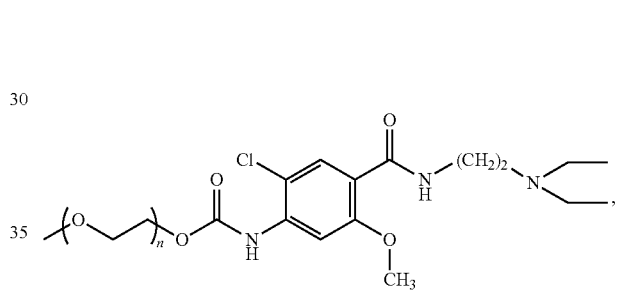

(wherein n is an integer of from 1 to 30, inclusive);

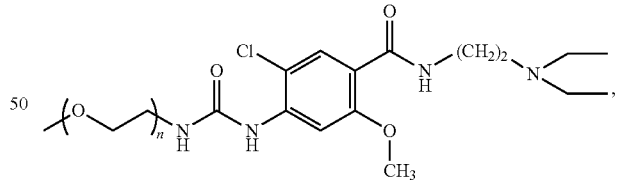

(wherein n is an integer of from 1 to 30, inclusive);

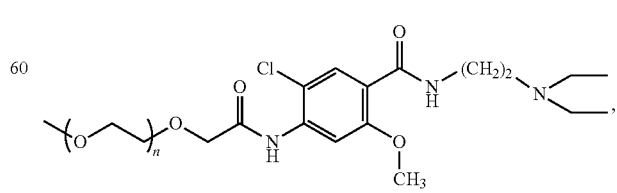

(wherein n is an integer of from 1 to 30, inclusive);

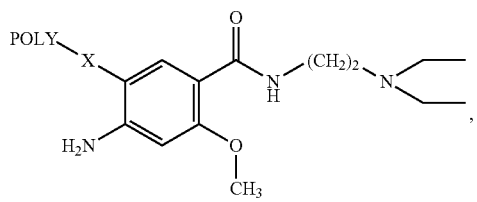

(wherein X is a spacer moiety and POLY is a water-soluble, non-peptidic oligomer);

Use of discrete oligomers (e.g., from a monodisperse or bimodal composition of oligomers, in contrast to relatively impure compositions) to form oligomer-containing compounds are preferred. For instance, a compound of the invention, when administered by any of a number of suitable administration routes, such as parenteral, oral, transdermal, buccal, pulmonary, or nasal, exhibits reduced penetration across the blood-brain barrier. It is preferred that the compounds of the invention exhibit slowed, minimal or effectively no crossing of the blood-brain barrier, while still crossing the gastro-intestinal (GI) walls and into the systemic circulation if oral delivery is intended. Moreover, the compounds of the invention maintain a degree of bioactivity as well as bioavailability in comparison to the bioactivity and bioavailability of the compound free of all oligomers.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

For compounds whose degree of blood-brain barrier crossing ability is not readily known, such ability may be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses may be conducted, for example, by contract research organizations such as Absorption Systems, Exton, Pa.). In one example of the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatography with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., Ertl et al. (2000) *J. Med. Chem.* 43:3714-3717 and Kelder et al. (1999) *Pharm. Res.* 16:1514-1519.

With respect to the blood-brain barrier, the water-soluble, non-peptidic oligomer-containing compound of the invention exhibits a blood-brain barrier crossing rate that is reduced (or substantially eliminated) as compared to the crossing rate of the small molecule drug not attached to the water-soluble, non-peptidic oligomer. Exemplary reductions in blood-brain barrier crossing rates for the compounds described herein include reductions of: at least about 5%; at least about 10%; at least about 25%; at least about 30%; at least about 40%; at least about 50%; at least about 60%; at least about 70%; at least about 80%; or at least about 90%, when compared to the blood-brain barrier crossing rate of the corresponding compound lacking water-soluble, non-peptic oligomers. A preferred reduction in the blood-brain barrier crossing rate for a conjugate of the invention is at least about 20%.

Assays for determining whether a given compound (regardless of whether the compound includes a water-soluble, non-peptidic oligomer or not) can act as a benzamide-based compound are known and/or may be prepared by one of ordinary skill in the art and are further described infra.

Each of these (and other) benzamide-based compound moieties can be covalently attached (either directly or through one or more atoms) to a water-soluble, non-peptidic oligomer.

Exemplary molecular weights of a benzamide-based compound (prior to, for example, conjugation to a water-soluble, non-peptidic oligomer) include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300 Daltons.

The benzamide-based compound used in the invention, if chiral, may be obtained from a racemic mixture, or an optically active form, for example, a single optically active enantiomer, or any combination or ratio of enantiomers (e.g., scalemic and racemic mixtures). In addition, the benzamide-based compound may possess one or more geometric isomers. With respect to geometric isomers, a composition can comprise a single geometric isomer or a mixture of two or more geometric isomers. A benzamide-based compound for use in the present invention can be in its customary active form, or may possess some degree of modification. For example, the benzamide-based compound may have a targeting agent, tag, or transporter attached thereto, prior to or after covalent attachment of an oligomer. Alternatively, the benzamide-based compound may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the benzamide-based compound does not include attachment to a lipophilic moiety.

The benzamide-based compound for coupling to a water-soluble, non-peptidic oligomer possesses a free hydroxyl, carboxyl, thio, amino group, or the like (i.e., "handle") suitable for covalent attachment to the oligomer. In addition, the benzamide-based compound may be modified by introduction of a reactive group, preferably by conversion of one of its existing functional groups to a functional group suitable for formation of a stable covalent linkage between the oligomer and the drug.

Each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; a-hydroxy acid, such as lactic acid or glycolic acid; phosphazene, oxazoline, amino acids, carbohydrates such as monosaccharides, alditol such as mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, the water-soluble, non-peptidic oligomer can be linear, branched, or forked. Most typically, the water-soluble, non-peptidic oligomer is linear or is branched, for example, having one branch point. Although much of the discussion herein is focused upon polyethylene oxide) as an illustrative oligomer, the discussion and structures presented herein can be readily extended to encompass any water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble, non-peptidic polymer includes $CH_3$—$(OCH_2CH_2)_n$—, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weight of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the benzamide-based compound (in contrast to the stepwise addition of one or more monomers to effectively "grow" the oligomer onto the benzamide-based compound), it is preferred that the composition containing an activated form of the water-soluble, non-peptidic oligomer be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., *J. Org. Chem.*, 6870-6873 (1999), WO 02/098949, and U.S. Patent Application Publication No. 2005/0136031.

The spacer moiety (the linkage through which the water-soluble, non-peptidic polymer is attached to the benzamide-based compound) may be a single bond, a single atom, such as an oxygen atom or a sulfur atom, two atoms, or a number of atoms. A spacer moiety is typically but is not necessarily linear in nature. The spacer moiety, "X," is preferably hydrolytically stable, and is also preferably enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R_{drug}$, is considered to have a chain length of 3 atoms (—NH—C(O)—NH—). In selected embodiments, the linkage does not comprise further spacer groups.

In some instances, the spacer moiety (e.g., "X" in various structures provided herein) comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) other atoms, as described further below.

More specifically, in selected embodiments, a spacer moiety (e.g., "X" in various structures provided herein) may be any of the following: "—" (i.e., a covalent bond, that may be stable or releasable, between the benzamide-based compound and the water-soluble, non-peptidic oligomer), —O—, —NH—, —S—, —C(O)—, —C(O)O—, —OC(O)—, —CH$_2$—C(O)O—, —CH$_2$—OC(O)—, —C(O)O—CH$_2$—, —OC(O)—CH$_2$—, C(O)—NH, —NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —CH$_2$—CH$_2$—CH$_2$—CH$_2$—, —CH$_2$—CH$_2$—CH$_2$—C(O)—NH—CH$_2$—CH$_2$—, —CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—N H—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl. Additional spacer moieties include, acylamino, acyl, aryloxy, alkylene bridge containing between 1 and 5 inclusive carbon atoms, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, 4-(methoxy-lower alkyl)-1-piperizinyl, and guanidine. In some instances, a portion or a functional group of the drug compound may be modified or removed altogether to facilitate attachment of the oligomer. In some instances, it is preferred that X is not an amide, i.e., —CONR— and —RNCO—.

For purposes of the present invention, however, a group of atoms is not considered a linkage when it is immediately adjacent to an oligomer segment, and the group of atoms is the same as a monomer of the oligomer such that the group would represent a mere extension of the oligomer chain.

The spacer moiety between the water-soluble, non-peptidic oligomer and the small molecule is formed by reaction of a functional group on a terminus of the oligomer (or nascent oligomer when it is desired to "grow" the oligomer onto the benzamide-based compound) with a corresponding functional group within the benzamide-based compound. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g., succinimidyl or benzotriazolyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: CH$_3$O—(CH$_2$—CH$_2$—O)$_n$—(CH$_2$)$_p$—C(O)H, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4.

The termini of the water-soluble, non-peptidic oligomer not bearing a functional group may be capped to render it unreactive. When the oligomer includes a further functional group at a terminus other than that intended for formation of a conjugate, that group is either selected such that it is unreactive under the conditions of formation of the spacer moiety (e.g., "X") or it is protected during the formation of the spacer moiety (e.g., "X").

As stated above, the water-soluble, non-peptidic oligomer includes at least one functional group prior to conjugation. The functional group comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, 2-thiazolidine thione, etc., as well as hydrates or protected derivatives of any of the above moieties (e.g., aldehyde hydrate, hemiacetal, acetal, ketone hydrate, hemiketal, ketal, thioketal, thioacetal).

An "activated derivative" of a carboxylic acid refers to a carboxylic acid derivative that reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the benzamide-based compound may not have a functional group suited for conjugation. In this instance, it is possible to modify (or "functionalize") the "original" benzamide-based compound so that it does have a functional group suited for conjugation. For example, if the benzamide-based compound has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of benzamide-based compound bearing a carboxyl group wherein the carboxyl group-bearing benzamide-based compound is coupled to an amino-terminated oligomeric ethylene glycol, to provide a conjugate having an amide group covalently linking the benzamide-based compound to the oligomer. This can be performed, for example, by combining the carboxyl group-bearing benzamide-based compound with the amino-terminated oligomeric ethylene glycol in the presence of a coupling reagent, (such as dicyclohexylcarbodiimide or "DCC") in an anhydrous organic solvent.

Further, it is possible to prepare a conjugate of a benzamide-based compound bearing a hydroxyl group wherein the hydroxyl group-bearing benzamide-based compound is coupled to an oligomeric ethylene glycol halide to result in an ether (—O—) linked conjugate. This can be performed, for example, by using sodium hydride to deprotonate the hydroxyl group followed by reaction with a halide-terminated oligomeric ethylene glycol.

Further, it is possible to prepare a conjugate of a benzamide-based compound bearing a hydroxyl group wherein the hydroxyl group-bearing benzamide-based compound is coupled to an oligomeric ethylene glycol bearing an haloformate group [e.g., CH$_3$(OCH$_2$CH$_2$)$_n$OC(O)-halo, where halo is chloro, bromo, iodo] to result in a carbonate [—O—C(O)—O—] linked small molecule conjugate. This can be performed, for example, by combining a benzamide-based compound and an oligomeric ethylene glycol bearing a haloformate group in the presence of a nucleophilic catalyst (such as 4-dimethylaminopyridine or "DMAP") to thereby result in the corresponding carbonate-linked conjugate.

In another example, it is possible to prepare a conjugate of a benzamide-based compound bearing a ketone group by first reducing the ketone group to form the corresponding hydroxyl group. Thereafter, the benzamide-based compound now bearing a hydroxyl group can be coupled as described herein.

In still another instance, it is possible to prepare a conjugate of a benzamide-based compound bearing an amine group. In one approach, the amine group-bearing benzamide-based compound and an aldehyde-bearing oligomer are dissolved in a suitable buffer after which a suitable reducing agent (e.g., NaCNBH$_3$) is added. Following reduction, the result is an amine linkage formed between the amine group of the amine group-containing benzamide-based compound and the carbonyl carbon of the aldehyde-bearing oligomer.

In another approach for preparing a conjugate of a benzamide-based compound bearing an amine group, a carboxylic acid-bearing oligomer and the amine group-bearing benzamide-based compound are combined, in the presence of a coupling reagent (e.g., DCC). The result is an amide linkage formed between the amine group of the amine group-containing benzamide-based compound and the carbonyl of the carboxylic acid-bearing oligomer.

While it is believed that the full scope of the compounds disclosed herein behave as described, an optimally sized oligomer can be identified as follows.

First, an oligomer obtained from a monodisperse or bimodal water soluble oligomer is conjugated to the benzamide-based compound. Preferably, the drug is orally bioavailable, and on its own, exhibits a non-negligible blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. Preferably, the compounds according to the invention maintain a significant degree of bioactivity relative to the parent drug, i.e., greater than about 30% of the bioactivity of the parent drug, or even more preferably, greater than about 50% of the bioactivity of the parent drug.

The above steps are repeated one or more times using oligomers of the same monomer type but having a different number of subunits and the results compared.

For each conjugate whose ability to cross the blood-brain barrier is reduced in comparison to the non-conjugated small molecule drug, its oral bioavailability is then assessed. Based upon these results, that is to say, based upon the comparison of conjugates of oligomers of varying size to a given small molecule at a given position or location within the small molecule, it is possible to determine the size of the oligomer most effective in providing a conjugate having an optimal balance between reduction in biological membrane crossing, oral bioavailability, and bioactivity. The small size of the oligomers makes such screenings feasible and allows one to effectively tailor the properties of the resulting conjugate. By making small, incremental changes in oligomer size and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

To determine whether the benzamide-based compound or a compound of the invention (e.g., a conjugate of a benzamide-based compound and a water-soluble, non-peptidic oligomer) has activity as a benzamide-based compound therapeutic, it is possible to test such a compound. For example, the activity of a compound of interest can be tested using an in vitro functional assay for the relevant receptor, transporter, or other specific molecular target of interest. With respect to pseudoephedrine-type activity, for example, such activity can be tested by measuring the release of norepinephrine from norepinephrine transporter (NET)-expressing cells in culture.

The compounds of the invention may be administered per se or in the form of a pharmaceutically acceptable salt, and any reference to the compounds of the invention herein is intended to include pharmaceutically acceptable salts. If used, a salt of a compound as described herein should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the compound with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulfonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

The present invention also includes pharmaceutical preparations comprising a compound as provided herein in combination with a pharmaceutical excipient. Generally, the compound itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, maltitol, lactitol, xylitol, sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines, fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the compound of the invention in the composition will vary depending on a number of factors, but will optimally be a therapeutically effective dose when the composition is stored in a unit dose container. A therapeutically effective dose can be determined experimentally by repeated administration of increasing amounts of the compound in order to determine which amount produces a clinically desired endpoint.

The amount of any individual excipient in the composition will vary depending on the activity of the excipient and particular needs of the composition. The optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., *acacia* sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethylcellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (as a lyophilizate or precipitate, which can be in the form of a powder or cake), as well as formulations prepared for injection, which are liquid and require the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, normally being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The compounds of the invention can also be administered through the skin using conventional transdermal patch or other transdermal delivery system, wherein the conjugate is contained within a laminated structure that serves as a drug delivery device to be affixed to the skin. In such a structure, the compound is contained in a layer, or "reservoir," underlying an upper backing layer. The laminated structure can contain a single reservoir, or it can contain multiple reservoirs.

The compounds of the invention can also be formulated into a suppository for rectal administration. With respect to suppositories, the compound is mixed with a suppository base material which is (e.g., an excipient that remains solid at room temperature but softens, melts or dissolves at body temperature) such as coca butter (*theobroma* oil), polyethylene glycols, glycerinated gelatin, fatty acids, and combinations thereof. Suppositories can be prepared by, for example, performing the following steps (not necessarily in the order presented): melting the suppository base material to form a melt; incorporating the compound (either before or after melting of the suppository base material); pouring the melt into a mold; cooling the melt (e.g., placing the melt-containing mold in a room temperature environment) to thereby form suppositories; and removing the suppositories from the mold.

In some embodiments of the invention, the compositions comprising the compounds of the invention may further be incorporated into a suitable delivery vehicle. Such delivery vehicles may provide controlled and/or continuous release of the compounds and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), *Rhodotorula* yeast cell particles (YCP). Yeast cells such as *S. cerevisiae* and *Rhodotorula* species are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495, 4,810,646, 4,992,540, 5,028,703 and 5,607,677, and U.S. Patent Application Publication Nos. 2005/0281781 and 2008/0044438.

The invention also provides a method for administering a compound of the invention as provided herein to a patient suffering from a condition that is responsive to treatment with the compound. The method comprises administering, generally orally, a therapeutically effective amount of the compound (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of a particular compound of the invention. Those of ordinary skill in the art appreciate which conditions a specific compound can effectively treat. Exemplary conditions include gastroparesis. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given compound of the invention (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are incorporated by reference in their entireties. In the event of an inconsistency between the teachings of this specification and the art incorporated by reference, the meaning of the teachings and definitions in this specification shall prevail (particularly with respect to terms used in the claims appended herein). For example, where the present application and a publication incorporated by reference defines the same term differently, the definition of the term shall be preserved within the teachings of the document from which the definition is located.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All non-PEG chemical reagents referred to in the appended examples are commercially available unless otherwise indicated. The preparation of PEG-mers is described in, for example, U.S. Patent Application Publication No. 2005/0136031.

$^1$H NMR (nuclear magnetic resonance) data was generated by an NMR spectrometer.

Example 1

Synthesis of "mPEG$_n$-N-Metoclopramide"—Approach A

Compounds designated as "mPEG$_n$-N-metoclopramide" were prepared using a first approach. This first approach is represented schematically below.

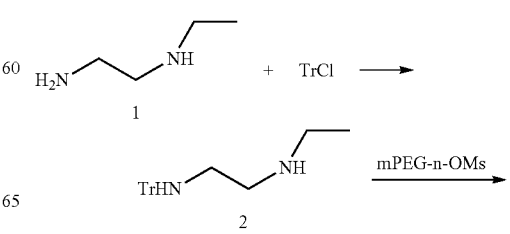

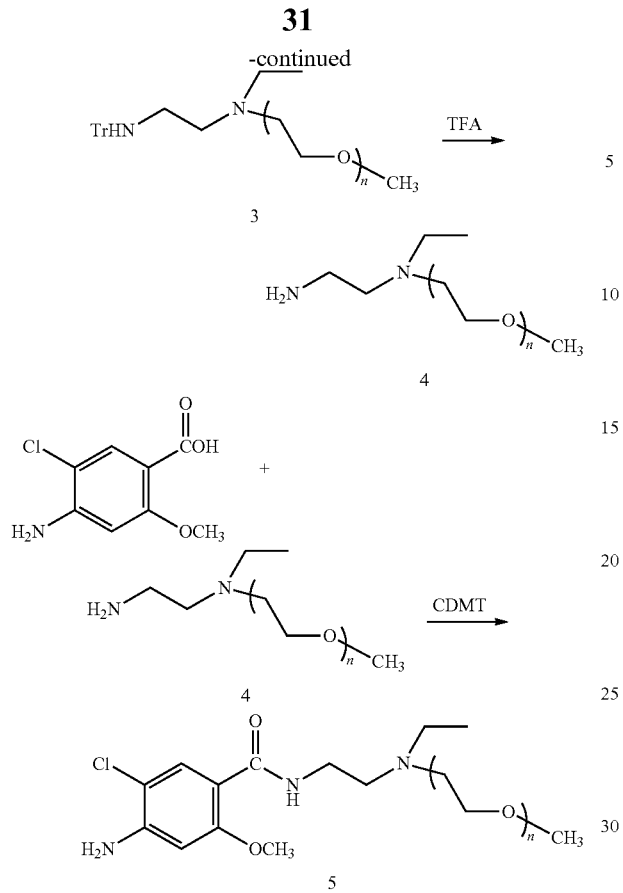

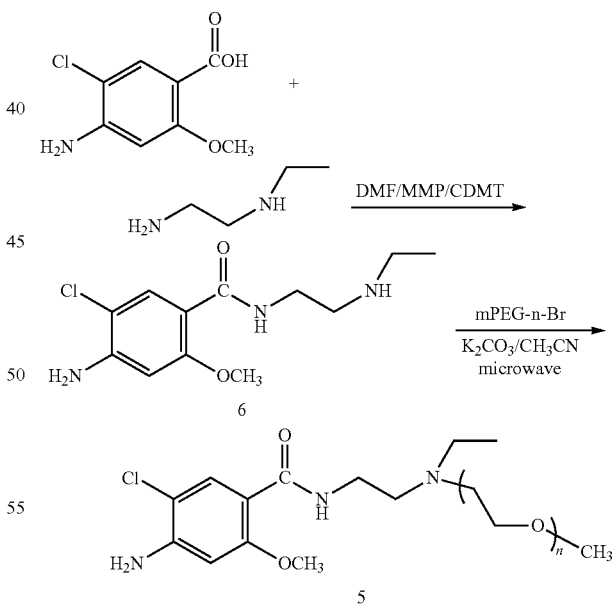

Synthesis of Trityl-N-Ethylethylenediamine (Compound 2)

Trityl chloride (~3.45 g, ~12.5 mmol) was slowly added into N-ethylethlenediamine (~1.1 g, ~12.5 mmol) DCM (methylene chloride) solution with stirring. After the reaction mixture was stirred at room temperature overnight (~23 hours), HPLC indicated that the reaction was complete. After Biotage silica gel chromatography was performed (EtOAc/MeOH), Compound 2 was obtained as a white solid (~3.5 g, ~85% isolated yield), and the product was confirmed by proton NMR.

Synthesis of $mPEG_6$-N-Trityl-N-Ethylethylenediamine (Compound 3, n=6)

The acetonitrile solution of $mPEG_6$-OMs (~0.66 g, ~1.76 mmol, wherein Ms is mesylate), DIPEA (~0.66 g, ~4.81 mmol) and Compound 2 (~0.53 g, ~1.60 mmol) were heated at 100° C. under microwave for ~8 hours. HPLC indicated that the reaction was complete. After Biotage silica gel chromatography (EtOAc/MeOH) was performed, Compound 3 (n=6) was obtained as a colorless liquid (~0.51 g, ~52% isolated yield), and the product was confirmed by LC-MS (calc: 608.0. found: 608.0).

Synthesis of $mPEG_6$-N-Ethylethylenediamine (Compound 4, n=6)

TFA mL) was added into a DCM solution of $mPEG_6$-N-trityl-N-ethylethylenediamine (~0.51 g, ~0.83 mmol), the solution was stirred at room temperature overnight (~17 hours). HPLC indicated that the deprotection was complete. After the DCM solvent was removed, the product mixture was dissolved in 0.1N HCl and the product solution was washed with EtOAc twice. The pH of the solution was adjusted to ~9 with $Na_2CO_3$ and product extracted with DCM twice. After work up, a colorless liquid was obtained (~0.26 g, ~85% isolated yield), and proton NMR confirmed that it was pure $mPEG_6$-N-ethylethylene diamine.

Synthesis of $mPEG_6$-N-Metoclopramide (Compound 5, n=6)

To a DMF solution of 4-amino-5-chloro-2-methoxybenzoic acid (~70 mg, ~0.35 mmol) and methylmorpholine (~127 mg, ~0.35 mmol), CDMT (~61 mg, ~0.35 mmol) was added, and the solution was stirred at room temperature for ~30 minutes. Thereafter, $mPEG_6$-N-ethylethylenediamine (~127 mg, ~0.35 mmol) was added. After ~18 hours, HPLC indicated that the reaction was complete. DCM was added to the reaction mixture and the DCM solution was washed with 0.1N NaOH/NaCl solution three times. After all solvents were removed, the product mixture was loaded on a silica gel column and eluted with EtOAc/Methanol in a Biotage. A colorless liquid was obtained (~70 mg, ~0.13 mmol, ~37% isolated yield). Both HPLC and proton NMR confirmed that it was the desired $mPEG_6$-N-metoclopramide (Compound 5, n=6), which was also confirmed by LC-MS (calc: 549.3. found: 549.3).

Using "Approach A," $mPEG_n$-N-metoclopramide compounds where n is equal to a number other than 6 (e.g, 1-5 and 6-15) can be prepared by substituting $mPEG_6$-OMs (e.g., with $mPEG_{1-5\ and\ 6-15}$-OMs, respectively).

Example 2

Synthesis of "$mPEG_1$-N-Metoclopramide"—Approach B

Compounds designated as $mPEG_n$-N-metoclopramide were prepared using a second approach. This second approach is represented schematically below.

Synthesis of Ethylethylenediamine-4-Amino-5-Chloro-2-Methoxybenzoic Acid Amide (Compound 6)

To a DMF solution of 4-amino-5-choro-2-methoxybenzoic acid (~1.8 g, ~8.9 mmol) and methylmorpholine (~2.7 g, ~26.8 mmol), CDMT was added (~1.6 g, ~8.9 mmol) and the reaction mixture was stirred at room temperature for ~1 hour. Thereafter, N-ethylethlenediamine (~1.6 g, ~17.9 mmol) was then added. The reaction mixture was stirred at room temperature overnight (~19 h), and HPLC indicated that the reaction was complete. DCM was added to the reaction mixture and the DCM solution was washed with 0.1N NaOH/NaCl aqueous solution three times. After all solvents were removed, the product mixture was loaded on a silica gel column and eluted with DCM/Methanol in a Biotage. A white solid was obtained (~1.5 g, ~5.5 mmol, ~62% isolated yield). LC-MS: calc: 271.1. found: 271.1. Proton NMR also confirmed that it was the desired ethylethlenediamine-4-amino-5-chloro-2-methoxybenzoic acid amide (Compound 6).

Synthesis of $mPEG_1$-N-Metoclopramide (Compound 5, n=1)

A THF solution of 2-bromoethyl methyl ether (~0.77 g, ~5.5 mmol), Compound 6 (~0.50 g, ~1.8 mmol) and excess $K_2CO_3$ were heated at 100° C. under microwave for ~3 hours. HPLC indicated that the product was formed in ~50% yield. After solvent removal, the residue was dissolved in 0.1N HCl solution. The product solution was washed three times with DCM and thereafter $K_2CO_3$ was added to adjust the pH to ~9 and for extraction with DCM for three times. After solvent evaporation, the residue was chromatographed with a Biotage using DCM/TEA/methanol solvents. Pure $mPEG_1$-N-metoclopramide was obtained as a semi-solid (~122 mg, ~0.37 mmol, ~20% isolated yield). The product was confirmed by both HPLC and proton NMR.

Example 3

Synthesis of $mPEG_2$-N-Metoclopramide

Using an approach generally corresponding to the second approach described in Example 2, "$mPEG_2$-N-metoclopramide" (Compound 5, n=2) was prepared.

A THF solution of 1-bromo-2-(2-methoxyethoxy)ethane (~0.67 g, ~3.7 mmol), compound (Compound 6) (~0.50 g, ~1.8 mmol) and excess $K_2CO_3$ were heated at 100° C. under microwave for ~4 hours. HPLC indicated that the product was formed in ~86% yield. After solvent removal, the residue was dissolved in 0.2N HCl solution. The product solution was washed three times with DCM and thereafter $K_2CO_3$ was added to adjust the pH to ~9 and for extraction with DCM for three times. After solvent evaporation, the residue was chromatographed with a Biotage using DCM/TEA/methanol solvents. Pure $mPEG_2$-N-metoclopramide was obtained as a semi-solid (~370 mg, ~0.99 mmol, ~54% isolated yield). The product was confirmed by both HPLC and proton NMR.

Example 4

Synthesis of $mPEG_3$-N-Metoclopramide

Using an approach generally corresponding to the second approach described in Example 2, "$mPEG_3$-N-metoclopramide" (Compound 5, n=3) was prepared.

An acetonitrile solution of $mPEG_3$-OMs (~0.51 g, ~2.1 mmol), Compound 6 (~0.38 g, ~1.4 mmol) and excess $K_2CO_3$ were heated at 100° C. under microwave for ~10 hours. HPLC indicated that the product was formed in ~60% yield. After solvent removal, the residue was dissolved in 0.2N HCl solution. The product solution was washed three times with DCM and thereafter $K_2CO_3$ was added to adjust the pH to ~9 and for extraction with DCM for three times. After solvent evaporation, the residue was chromatographed with a Biotage using DCM/TEA/methanol solvents. Pure $mPEG_3$-N-metoclopramide was obtained as a sticky liquid (~260 mg, ~0.62 mmol, ~45% isolated yield). The product was confirmed by both HPLC and proton NMR.

Example 5

Synthesis of $mPEG_4$-N-Metoclopramide

Using an approach generally corresponding to the second approach described in Example 2, "$mPEG_4$-N-metoclopramide" (Compound 5, n=4) was prepared.

A THF solution of $mPEG_4$-Br (~1.0 g, ~3.7 mmol), Compound 6 (~0.50 g, ~1.8 mmol) and excess $K_2CO_3$ were heated at 100° C. under microwave for ~4 hours. HPLC indicated that the product was formed in ~70% yield. After solvent removal, the residue was dissolved in 0.2N HCl solution. The product solution was washed three times with DCM and thereafter $K_2CO_3$ was added to adjust the pH to ~9 and for extraction with DCM for three times. After solvent evaporation, the residue was chromatographed with a Biotage with DCM/TEA/methanol solvents. Pure $mPEG_4$-N-metoclopramide was obtained as a liquid (~277 mg, ~0.60 mmol, ~33% isolated yield). The product was confirmed by both HPLC and proton NMR.

Example 6

Synthesis of $mPEG_5$-N-Metoclopramide

Using an approach generally corresponding to the second approach described in Example 2, "$mPEG_5$-N-metoclopramide" (Compound 5, n=5) was prepared.

An acetonitrile solution of $mPEG_5$-OMs (~0.22 g, ~0.66 mmol), Compound (6) (~0.90 g, ~0.33 mmol) and excess $K_2CO_3$ was heated at 160° C. under microwave for ~1.5 hours. HPLC indicated that the product was formed in ~60% yield. After solvent removal, the residue was dissolved in 0.1N HCl solution. The product solution was washed three times with DCM and thereafter $K_2CO_3$ was added to adjust pH to ~9 and for extraction with DCM three times. After solvent evaporation, the residue was chromatographied with a Biotage with DCM/TEA/methanol solvents. Pure $mPEG_5$-N-metoclopramide was obtained as a sticky liquid (~73 mg, ~0.14 mmol, ~44% isolated yield). The product was confirmed by both HPLC and proton NMR.

Example 7

Synthesis of $mPEG_6$-N-Metoclopramide

Using an approach generally corresponding to the second approach described in Example 2, "$mPEG_6$-N-metoclopramide" (Compound 5, n=6) was prepared.

A THF solution of $mPEG_6$-Br (~0.66 g, ~1.8 mmol), Compound 6 (~0.25 g, ~0.92 mmol) and excess $K_2CO_3$ were heated at 100° C. under microwave for ~4 hours. HPLC indicated that the product was formed in ~70% yield. After solvent removal, the residue was dissolved in 0.2N HCl solution. The product solution was washed three times with DCM and thereafter $K_2CO_3$ was added to adjust the pH to ~9 and for extraction with DCM for three times. After solvent evaporation, the residue was chromatographed with a Biotage using DCM/TEA/methanol solvents. Pure $mPEG_6$-N-metoclopramide was obtained as a light yellow liquid (~249 mg, ~0.45 mmol, ~49% isolated yield). The product was confirmed by both HPLC and proton NMR.

Example 8

Synthesis of mPEG$_7$-N-Metoclopramide

Using an approach generally corresponding to the second approach described in Example 2, "mPEG$_7$-N-metoclopramide" (Compound 5, n=7) was prepared.

A THF solution of mPEG$_7$-Br (~1.4 g, ~3.4 mmol), Compound 6 (~0.46 g, ~1.7 mmol) and excess K$_2$CO$_3$ were heated at 100° C. under microwave for ~4 hours. HPLC indicated that the reaction was complete. After THF solvent removal, the residue was dissolved in 0.2N HCl solution. The product solution was washed three times with DCM and thereafter K$_2$CO$_3$ was added to adjust pH to ~9 and for extraction with DCM for three times. After solvent evaporation, the residue was chromatographed with a Biotage with DCM/TEA/methanol solvents. Pure mPEG$_7$-N-metoclopramide was obtained as a sticky liquid (~260 mg, ~0.44 mmol, ~26% isolated yield). The product was confirmed by both HPLC and proton NMR.

Example 9

Synthesis of mPEG$_8$-N-Metoclopramide

Using an approach generally corresponding to the second approach described in Example 2, "mPEG$_8$-N-metoclopramide" (Compound 5, n=8) was prepared.

A THF solution of mPEG$_8$-Br (~1.6 g, ~3.5 mmol), Compound 6 (~0.48 g, ~1.8 mmol) and excess K$_2$CO$_3$ were heated at 100° C. under microwave for ~3 hours. HPLC indicated that the product was formed in ~70% yield. After THF solvent removal, the residue was dissolved in 0.2N HCl solution. The product solution was washed three times with DCM and thereafter K$_2$CO$_3$ was added to adjust pH to ~9 and for extraction with DCM for three times. After solvent evaporation, the residue was chromatographed with DCM/TEA/methanol solvents in a Biotage. Pure mPEG$_8$-N-metoclopramide was obtained as a semi-solid (~350 mg, ~0.55 mmol, ~31% isolated yield). The product was confirmed by both HPLC and proton NMR.

Example 10

Synthesis of mPEG$_9$-N-Metoclopramide

Using an approach generally corresponding to the second approach described in Example 2, "mPEG$_9$-N-metoclopramide" (Compound 5, n=9) was prepared.

A THF solution of mPEG$_9$-Br (~1.4 g, ~2.9 mmol), Compound 6 (~0.40 g, ~1.5 mmol) and excess K$_2$CO$_3$ were heated at 100° C. under microwave for ~5 hours. HPLC indicated that the reaction was complete. After THF solvent removal, the residue was dissolved in 0.2N HCl solution. The product solution was washed three times with DCM and thereafter K$_2$CO$_3$ was added to adjust the pH to ~9 and for extraction with DCM for three times. After solvent evaporation, the residue was chromatographed with DCM/TEA/methanol solvents in a Biotage. Pure mPEG$_9$-N-metoclopramide was obtained as a semi-solid (~132 mg, ~0.19 mmol, ~13% isolated yield). The product was confirmed by both HPLC and proton NMR.

Example 11

Competition Binding Assay (Dopamine 2$_L$ Receptors)

Competition binding to [$^3$H] methylspiperone was performed to determine binding affinity of metoclopramide and conjugates to dopamine 2$_L$ ("D2$_L$") receptors. Serial dilutions of metoclopramide and conjugates were prepared in 100% DMSO. Membrane preparations of Hek-293 cells stably expressing D2$_L$ receptors were diluted in assay buffer (50 mM Tris-HCl, 10 mM MgCl$_2$, 120 mM NaCl) to a final concentration of 3 ug/well. [$^3$H] Methylspiperone was diluted in assay buffer to a final concentration of 0.4 nM. To start the assay, 1 uL of compound was added into 96-well v-bottom plates, followed by the addition of 50 uL of diluted membrane preparation, then finally diluted [$^3$H] Methylspiperone was added. The assay mixture was incubated for 60 minutes at room temperature with shaking. Following incubation, bound [$^3$H] methylspiperone on 5% PEI soaked GF/B filter plates using a Filtermate Harvester (Perkin Elmer) were then washed four times with ice cold wash buffer (50 mM Tris-HCl, pH 7.5). Filter plates were air dried for two minutes, and then 50 uL of MicroScint-20 was added into each well. Radioactivity counts were quantified using a Top Count plate reader (Perkin Elmer). Data was analyzed using one-site binding competition non-linear regression curve fitting on GraphPad Prism.

IC50 values for metoclopramide, and mPEG$_{1-9}$-N-metoclopramide (prepared in accordance with Examples 2 through 10, respectively) were determined in a one-site binding competition assay with [$^3$H]-methylspiperone, on membranes prepared from HEK 293 cells stably expressing dopamine 2$_L$ receptors. IC50 values determined were 8.42E-08 M for the metoclopramide, 2.33E-07 M for mPEG$_1$-N-metoclopramide, 1.36E-06 M for mPEG$_2$-N-metoclopramide, 3.45E-06 M for mPEG$_3$-N-metoclopramide, 3.26E-06 M for mPEG$_4$-N-metoclopramide, 8.29E-06 M for mPEG$_5$-N-metoclopramide, 7.75E-06 M for mPEG$_6$-N-metoclopramide, 1.16E-05 M for mPEG$_7$-N-metoclopramide, 6.79E-06 M for mPEG$_8$-N-metoclopramide, and 1.11 E-05 M for mPEG$_9$-N-metoclopramide. Fold change relative to parent compound were 2.8, 16.1, 41, 38.7, 98.5, 92.1, 137.3, 80.7, and 131.9 respectively. These results are also provided in Table 1. In a preliminary run that was not quality controlled, the IC50 values determined were 9.32E-07 M for metoclopramide (expected IC50=540 nM), 4.65E-06 M for mPEG$_3$-N-metoclopramide, 1.51E-05 M for mPEG$_5$-N-metoclopramide, and 1.31E-05 M for mPEG$_3$-N-metoclopramide. In all runs, haloperidol was run in the assay as a positive control with an IC50 value of 6.17E-09 (expected 1050=8.4, pKi=8.3).

TABLE 1

IC50 Values and Fold-change Relative to Parent Compound

| Description | IC50 [M] | IC50 [nM] | Fold-change Relative to Parent |
|---|---|---|---|
| Metoclopramide | 8.42E-08 | 84.17 | 1 |
| mPEG$_1$-N-Metoclopramide | 2.33E-07 | 233.4 | 2.8 |
| mPEG$_2$-N-Metoclopramide | 1.36E-06 | 1356 | 16.1 |
| mPEG$_3$-N-Metoclopramide | 3.45E-06 | 3451 | 41 |
| mPEG$_4$-N-Metoclopramide | 3.26E-06 | 3257 | 38.7 |
| mPEG$_5$-N-Metoclopramide | 8.29E-06 | 8289 | 98.5 |
| mPEG$_6$-N-Metoclopramide | 7.75E-06 | 7748 | 92.1 |
| mPEG$_7$-N-Metoclopramide | 1.16E-05 | 11560 | 137.3 |
| mPEG$_8$-N-Metoclopramide | 6.79E-06 | 6794 | 80.7 |
| mPEG$_9$-N-Metoclopramide | 1.11E-05 | 11100 | 131.9 |
| Haloperidol | 6.17E-09 | 6.17 | NA |

Example 12

Competition Binding Assay (Serotonin 4B Receptors)

Competition binding to [$^3$H] GR113808 (a selective antagonist with a high affinity at the Serotonin 4 receptor, i.e., 5HT4 receptor, Gale et al. (1994) *Br J Pharmacol* 111(1): 332-8) was performed to determine binding affinity of metoclopramide and conjugates to 5HT4B receptors. Serial dilutions of metoclopramide and conjugates were prepared in 100% DMSO. Membrane preparations of Hek-293 cells stably expressing 5HT4 receptors were diluted in assay buffer (50 mM Tris-HCl, 5 mM $MgCl_2$, 1 mM EDTA) to a final concentration of 2.5 ug/well. [$^3$H] GR113808 was diluted in assay buffer to a final concentration of 2 nM. To start the assay, 1 uL of compound was added into 96-well v-bottom plates, followed by the addition of 50 uL of diluted membrane preparation, then finally diluted [$^3$H] GR113808 was added. The assay mixture was incubated for 60 minutes at room temperature with shaking. Following incubation, bound [$^3$H] GR113808 on 5% PEI soaked GF/B filter plates using a Filtermate Harvester (Perkin Elmer) were then washed four times with ice cold wash buffer (50 mM Tris-HCl, pH 7.5). Filter plates were air dried for two minutes, and then 50 uL of MicroScint-20 was added into each well. Radioactivity counts were quantified using a Top Count plate reader (Perkin Elmer). Data was analyzed using one-site binding competition non-linear regression curve fitting on GraphPad Prism.

IC50 values for metoclopramide, and conjugates, $mPEG_{1-9}$-N-metoclopramide (prepared in accordance with Examples 2 through 10, respectively) were determined in a one-site binding competition assay with [$^3$H]-GR113808, on membranes prepared from HEK 293 cells stably expressing $5HT4_B$ receptors (serotonin 4B receptors). IC50 values determined were 1.52E-05 M for the metoclopramide, 1.97E-05 M for $mPEG_1$-N-metoclopramide, 2.97E-05 M for $mPEG_2$-N-metoclopramide, 3.18E-05 M for $mPEG_3$-N-metoclopramide, 3.07E-05 M for $mPEG_4$-N-metoclopramide, 5.81E-05 M for $mPEG_5$-N-metoclopramide, 5.78E-05 M for $mPEG_6$-N-metoclopramide, 1.33E-04 M for $mPEG_7$-N-metoclopramide, 1.81E-04 M for $mPEG_8$-N-metoclopramide, and 2.02E-04 M for $mPEG_9$-N-metoclopramide. Fold change relative to parent compound are 1.3, 2.0, 2.1, 2.0, 3.8, 3.8, 8.8, 11.9, and 13.3 respectively. Tropisetron was run in the assay as a positive control with an IC50 value of 9.10E-09 (pKi=8.5-8.8). Non-specific binding was determined with 10 uM tropisetron. The conjugates did not reach 100% inhibition even at the highest concentration (5.0E-3 M), which was the maximum limit. These results are also provided in Table 2.

TABLE 2

IC50 values and fold-change relative to parent compound

| Description | IC50 [M] | IC50 [nM] | Fold-change Relative to Parent |
|---|---|---|---|
| Metoclopramide | 1.52E-05 | 15210 | 1.0 |
| $mPEG_1$-N-Metoclopramide | 1.97E-05 | 19710 | 1.3 |
| $mPEG_2$-N-Metoclopramide | 2.97E-05 | 29700 | 2.0 |
| $mPEG_3$-N-Metoclopramide | 3.18E-05 | 31770 | 2.1 |
| $mPEG_4$-N-Metoclopramide | 3.07E-05 | 30660 | 2.0 |
| $mPEG_5$-N-Metoclopramide | 5.81E-05 | 58110 | 3.8 |
| $mPEG_6$-N-Metoclopramide | 5.78E-05 | 57830 | 3.8 |
| $mPEG_7$-N-Metoclopramide | 1.33E-04 | 133300 | 8.8 |
| $mPEG_8$-N-Metoclopramide | 1.81E-04 | 181100 | 11.9 |
| $mPEG_9$-N-Metoclopramide | 2.02E-04 | 201900 | 13.3 |

Example 13

Competition Binding Assay (Serotonin 3a Receptors)

Competition binding to [$^3$H] GR 65630 was performed to determine binding affinity of metoclopramide and conjugates to 5HT3 receptors. Serial dilutions of metoclopramide and conjugates were prepared in 100% DMSO. Membrane preparations of Hek-293 cells stably expressing 5HT3 receptors were diluted in assay buffer (50 mM Tris-HCl, 5 mM $MgCl_2$, 1 mM EDTA) to a final concentration of 2.5 ug/well. [$^3$H] GR 65630 was diluted in assay buffer to a final concentration of 2 nM. To start the assay, 1 uL of compound was added into 96-well v-bottom plates, followed by the addition of 50 uL of diluted membrane preparation, then finally diluted [$^3$H] GR 65630 was added. The assay mixture was incubated for 60 minutes at room temperature with shaking. Following incubation, bound [$^3$H] GR 65630 on 5% PEI soaked GF/B filter plates using a Filtermate Harvester (Perkin Elmer) were then washed four times with ice cold wash buffer (50 mM Tris-HCl, pH 7.5). Filter plates were air dried for two minutes, and then 50 uL of MicroScint-20 was added into each well. Radioactivity counts were quantified using a Top Count plate reader (Perkin Elmer). Data was analyzed using one-site binding competition non-linear regression curve fitting on GraphPad Prism.

IC50 values for metoclopramide, and conjugates, $mPEG_{3, 5\ and\ 6}$-N-metoclopramide (prepared in accordance with Examples 4, 6 and 7, respectively) were determined in a one-site binding competition assay with [$^3$H]-GR65630, on membranes prepared from HEK 293 cells stably expressing $5HT3_A$ receptors (serotonin 3A receptors). IC50 values determined were 6.86E-06 M (pKi=5.9-6.4) for metoclopramide, 1.60E-04 M for $mPEG_3$-N-metoclopramide, 1.07E-03 M for $mPEG_5$-N-metoclopramide, and 8.85E-04 M for $mPEG_6$-N-metoclopramide. Fold change relative to parent compound were 23, 156, and 129 respectively. Tropisetron was run in the assay as a positive control with an IC50 value of 9.10E-09 (pKi=8.5-8.8). Non-specific binding was determined with 10 uM tropisetron. The conjugates did not reach 100% inhibition even at the highest concentration (5.0E-3 M), which was the maximum limit. These results are also provided in Table 3.

TABLE 3

IC50 Values and Fold-change Relative to Parent Compound

| Description | IC50 [M] | IC50 [nM] | Fold-change Relative to Parent |
|---|---|---|---|
| Metoclopramide | 6.86E-06 | 6858 | 1 |
| $mPEG_3$-N-Metoclopramide | 1.60E-04 | 159800 | 23 |
| $mPEG_5$-N-Metoclopramide | 1.07E-03 | 1073000 | 156 |
| $mPEG_6$-N-Metoclopramide | 8.85E-04 | 885000 | 129 |
| Tropisetron | 9.10E-09 | 9.10 | NA |

Example 14

Arrestin Functional Assay (Dopamine)

The interaction of β-arrestin with activated dopamine $2_S$ ("$D2_S$") receptor in CHO-K1 cells expressing dopamine $2_S$ receptor was determine as a measure of the functional activity of metoclopramide and conjugates against dopamine $2_S$ ("$D2_S$") receptor. PathHunter eXpressing β-Arrestin Human GPCR kit from DiscoveRx (product #95-0084E2) was used for this purpose and the antagonist dose response procedure was followed. Cells were thawed as per manufacturer's instructions and grown overnight at 37° C. in a 5% CO2 water jacketed incubator (approximately 30,000 cells per well). Stock solutions of metoclopramide and conjugates (antagonists) were prepared in 100% DMSO and thereafter 11-point 3-fold serial dilutions of were prepared in 22% DMSO in PBS. Concentration of each dilution was 22× of the final screening concentration. Each antagonist dilution (5 µl) was added per well and incubated at 37° C. for 30 minutes in a 37° C., 5% CO2 water jacketed incubator. Dopamine agonist (5 µl) at EC80 (400 nM) was added to respective wells and incubated for 90 minutes at 37° C. in a 5% CO2 water jacketed incubator. Finally, 55 µl of DiscoveRx detection reagent was added per well, incubated at RT for 60 minutes and luminescence was measured using the Perkin Elmer Victor X4 HTRF reader. Data analysis was done using GraphPad Prism, sigmoidal dose-response (variable slope) curve fitting.

IC50 values for metoclopramide, and mPEG$_{1-9}$-N-metoclopramide (prepared in accordance with Examples 2 through 10, respectively) were determined in the β-arrestin interaction assay in CHO-K1 cells expressing dopamine 2S receptor. IC50 values determined were 8.21 E-08 M for the metoclopramide, 3.45E-07 M for mPEG$_1$-N-metoclopramide, 7.86E-07 M for mPEG$_2$-N-metoclopramide, 2.05E-06 M for mPEG$_3$-N-metoclopramide, 3.04E-06 M for mPEG$_4$-N-metoclopramide, 3.62E-06 M for mPEG$_5$-N-metoclopramide, 4.27E-06 M for mPEG$_6$-N-metoclopramide, 8.18E-05 M for mPEG$_7$-N-metoclopramide, 5.53E-06 M for mPEG$_8$-N-metoclopramide, and 7.22E-06 M for mPEG$_9$-N-metoclopramide. Fold change relative to parent compound are 4.19, 9.57, 25, 37.03, 44.1, 52.05, 99.57, 67.4 and 87.6 respectively. These results are also provided in Table 4.

TABLE 4

IC50 values and fold-change relative to parent compound

| Description | IC50 [M] | IC50 [nM] | Fold-change Relative to Parent |
|---|---|---|---|
| Metoclopramide | 8.21E−08 | 82.17 | 1 |
| mPEG$_1$-N-Metoclopramide | 3.45E−07 | 345 | 4.19 |
| mPEG$_2$-N-Metoclopramide | 7.86E−07 | 786.5 | 9.57 |
| mPEG$_3$-N-Metoclopramide | 2.05E−06 | 2055 | 25 |
| mPEG$_4$-N-Metoclopramide | 3.04E−06 | 3043 | 37.03 |
| mPEG$_5$-N-Metoclopramide | 3.62E−06 | 3624 | 44.1 |
| mPEG$_6$-N-Metoclopramide | 4.27E−06 | 4277 | 52.05 |
| mPEG$_7$-N-Metoclopramide | 8.18E−06 | 8182 | 99.57 |
| mPEG$_8$-N-Metoclopramide | 5.53E−06 | 5539 | 67.4 |
| mPEG$_9$-N-Metoclopramide | 7.22E−06 | 7220 | 87.86 |

Example 15 cAMP Accumulation Assay (Serotonin 4 Receptors)

Accumulation of cAMP was determined in CHO-K1 cells stably expressing 5HT4 receptor as a measure of the functional activity of metoclopramide and conjugates against serotonin 4 receptor (5HT4). Serial dilutions of metoclopramide and conjugates were prepared in 100% DMSO. CHO-K1 cells stably expressing 5HT4 were purchased from Multispan as division-arrested, single use aliquots. Cells were thawed and grown overnight in a 37° C., 5% CO2 water jacketed incubator. Cells were harvested using Invitrogen Cell Dissociation Buffer, then centrifuged at 1200 rpm for five minutes. The supernatant was aspirated and cells were resuspended in assay buffer (PBS/0.5 mM IBMX) to a density of 1×10$^6$ cells/mL. Cells (25 µl) were added into a white half-area 96-well plate. Thirteen point serial dilutions of test compounds were done in assay buffer (PBS with 0.5 mM IBMX). Metoclopramide was used as a positive control for each assay. Compound (25 µl) was added to the cells in duplicate for each test concentration. Cells were incubated for one hour in a 37° C., 5% CO2 water jacketed incubator.

CisBio HTRF cAMP assay reagent was used for cAMP quantitation. Two hours after substrate addition, signal at 665/615 nm was measured using the Perkin Elmer Victor X4 HTRF reader. Data analysis was done using GraphPad Prism, sigmoidal dose-response (variable slope) curve fitting.

IC50 values for metoclopramide, and conjugates, mPEG$_{1\ and\ 4}$-N-metoclopramide (prepared in accordance with Examples 2 and 5, respectively) were determined in cAMP accumulation assay in CHO-K1 cells stably expressing 5HT4. IC50 values determined were 1.02E-06 M for metoclopramide, 1.59E-06 M for mPEG$_1$-N-metoclopramide, and 6.44E-07 M for mPEG$_4$-N-metoclopramide. Fold change relative to parent compound were 1.5 and 0.62 respectively. These results are also provided in Table 5.

TABLE 5

IC50 Values and Fold-change Relative to Parent Compound

| Description | IC50 [M] | IC50 [µM] | Fold-change Relative to Parent |
|---|---|---|---|
| Metoclopramide | 1.02E−06 | 1.02 | 1.0 |
| mPEG$_1$-N-Metoclopramide | 1.59E−06 | 1.59 | 1.5 |
| mPEG$_4$-N-Metoclopramide | 6.44E−07 | 0.64 | 0.62 |

Example 16

MetID determination

Cryopreserved human and Sprague-Dawley rat hepatocytes were thawed in a 37° C. water bath. Metoclopramide, mPEG$_1$-N-metoclopramide (from Example 2), mPEG$_4$-N-metoclopramide (from Example 5), mPEG$_8$-N-metoclopramide (from Example 9), and testosterone (positive control) were incubated with hepatocytes for up to 0, 1, and 4 hours in an incubator set at 37° C. and 5% CO2. The incubation mixtures consisted of 10 µM metoclopramide, mPEG$_1$-N-metoclopramide, mPEG$_4$-N-metoclopramide, mPEG$_8$-N-metoclopramide, or 200 µM testosterone and 1.0 million cells/mL hepatocytes in Williams' Medium E in a final incubation volume of 100 µL. Samples were obtained from separate plates for each time point during the incubation. At each sampling time, the plates were removed from the incubator, quenched by adding 100 µL cold acetonitrile, and placed in an ice bath until centrifugation at 4,000 rpm for 30 minutes at 4° C. Supernatanted were stored at or below ~70° C. until LC-MS/MS analysis could be conducted. The liquid chromatography system used was Agilent 1100 Autosampler, Binary Pump, DAD and Column Enclosure. Tandem mass spectrometry was conducted using a Thermo DECA XP MAX Ion Trap Mass Spectrometer. The ion source was Electrospray (+) and the LC column used was a Varian, Polaris 5 C18-A (250×2.1 mm, 5 micron) column.

Figure 2:
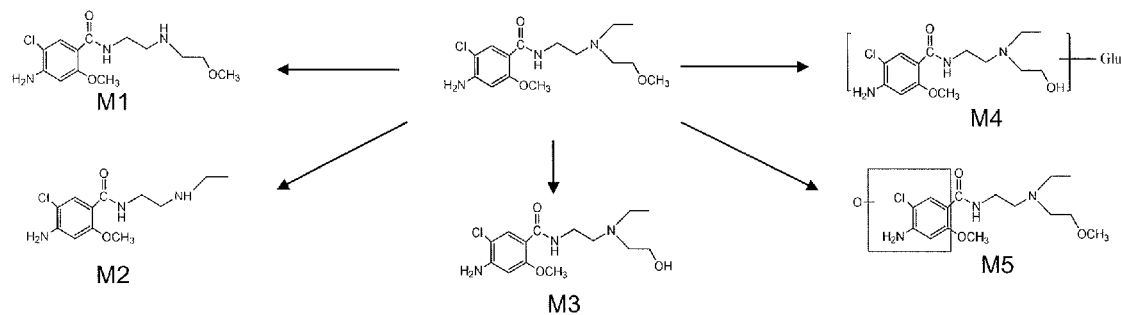
FIG. 2 is a schematic of the metabolic pathway of mPEG$_1$-N-metoclopramide as discussed in Example 16.
Figure 3:
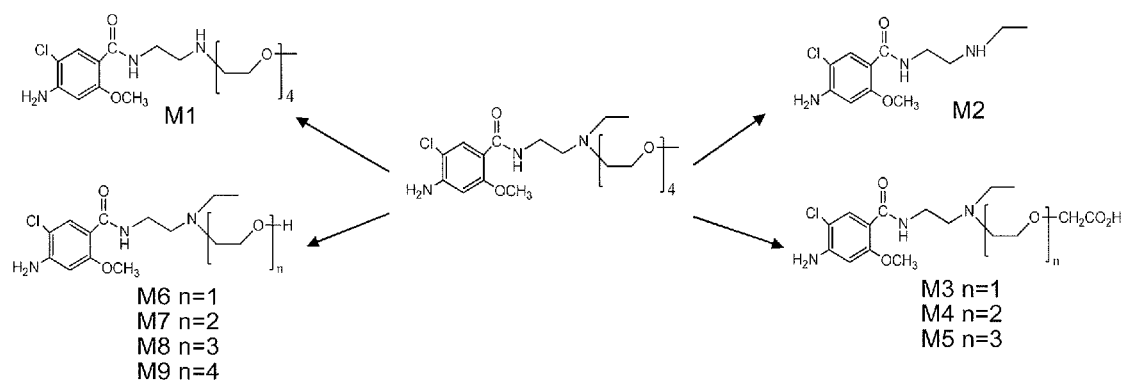
FIG. 3 is a schematic of the metabolic pathway of mPEG$_4$-N-metoclopramide as discussed in Example 16.
Figure 4:
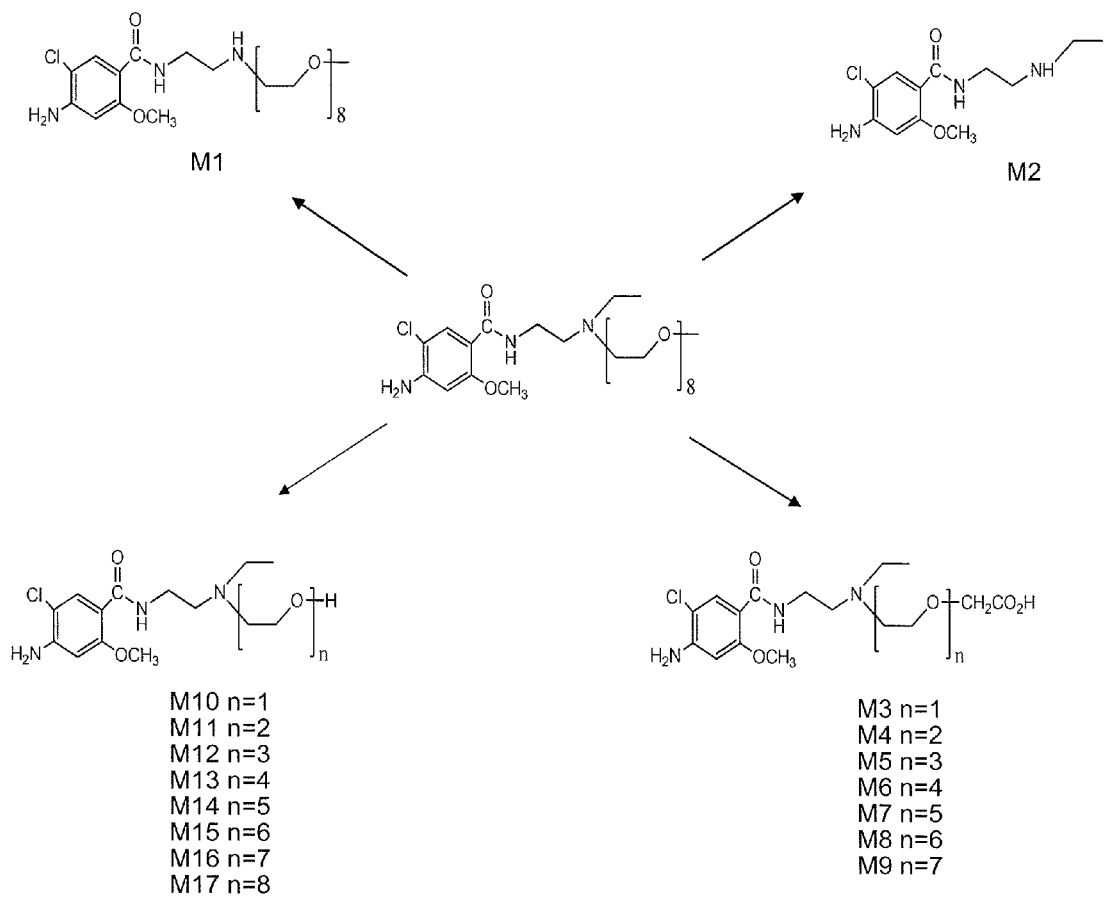
FIG. 4 is a schematic of the metabolic pathway of mPEG$_8$-N-metoclopramide as discussed in Example 16.

Metabolic pathways of metoclopramide and conjugates were determined in rat and human hepatocytes. N-dealkylation was the major metabolic pathway for metoclopramide in rats, and metabolism in human hepatocytes was minimal. FIG. 1 shows the metabolic pathway of metoclopramide. N-dealkylation was the major metabolic pathway for mPEG$_1$-N-metoclopramide and mPEG$_4$-N-metoclopramide in the rat, with low metabolism in human hepatocytes. Extensive metabolism was observed in rat hepatocytes after structural modification on metoclopromide. FIG. 2 and FIG. 3 show the metabolic pathway of for mPEG$_1$-N-metoclopramide and mPEG$_4$-N-metoclopramide, receptively. PEG chain modification was the major metabolic pathway for mPEG$_8$-N-netoclopramide in the rat, with only minor metabolism in human hepatocytes. N-dealkylation was less compared with metoclopromide. FIG. 4 shows the metabolic pathway of for mPEG$_8$-N-Metoclopramide. Table 6 shows the metabolite percentage. In this figure, different metabolites for each conjugate are denoted with the "M" and correspond to the designation provided in the figure for a given conjugate. For example, metabolite M1 for mPEG$_1$-N-metoclopramide in Table 6 corresponds to M1 in FIG. 2, metabolite M2 for mPEG$_4$-N-metoclopramide in Table 6 corresponds to M2 in FIG. 3 and metabolite M3 mPEG$_8$-N-metoclopramide in Table 6 corresponds to M3 in FIG. 4.

TABLE 6

Metabolism of Metoclopramide and Conjugates in Rat and Human Hepatocytes

| M | m/z | RT (min) | Human Hep 1 hr | Human Hep 4 hr | Rat Hep 1 hr | Rat Hep 4 hr |
|---|---|---|---|---|---|---|
| | | | % of Total Metabolism | | | |
| Metoclopromide | 300 | 18.5 | 96.8 | 97.5 | 87 | 61 |
| M1 | 316 | 16.3 | 3.2 | 2.5 | 2.2 | 1.1 |
| M2 | 272 | 15.6 | trace | trace | 10.8 | 18.9 |
| M3 | 259 | 20.1 | ND | ND | ND | 15.6 |
| M4 | 316 | 18.4 | ND | ND | trace | 3.4 |
| Others | | | <1.0% | <1.0% | <1.0% | <1.0% |
| mPEG$_1$-N-metoclopramide | 330 | 18.5 | 86.5 | 90.2 | 32.7 | <1.0 |
| M1 | 302 | 16.7 | 5.2 | 2.1 | 36.4 | 54.9 |
| M2 | 272 | 15.6 | 1.3 | 3.2 | 14.9 | 14.5 |
| M3 | 316 | 16.3 | 2.9 | trace | 13 | 7.5 |
| M4 | 492 | 14.9 | ND | ND | 2.00% | 15.5 |
| M5 | 346 | 19.7 | 2.1 | 2.5 | Trace | 3.6 |
| Others | | | <2.0% | <2.0% | <1.0% | <3.0% |
| mPEG$_4$-N-metoclopramide | 462 | 22.9 | 100 | 93.7 | 61.5 | 16.1 |
| M1 | 434 | 21.2 | ND | 2.6 | 6.7 | 14.4 |
| M2 | 272 | 15.7 | trace | 1.8 | 10.4 | 18.1 |
| M3 | 374 | 17.8 | ND | ND | 1.8 | 4 |
| M4 | 418 | 19.1 | ND | ND | 3.4 | 8.8 |
| M5 | 462 | 20.4 | ND | ND | 3.6 | 6.1 |
| M6 | 316 | 16.4 | ND | ND | trace | trace |
| M7 | 360 | 17.9 | ND | ND | 1.7 | 1.2 |
| M8 | 404 | 19 | ND | ND | trace | 1.5 |
| M9 | 448 | 20.1 | ND | 1.9 | 8.8 | 24.8 |
| Others | | | ND | ND | <2.0% | <5.0% |
| mPEG$_8$-N-metoclopramide | 638 | 25.63 | 100 | 94.8 | 83 | 43.5 |
| M1 | 610 | 24.1 | trace | 2.5 | 1.5 | 5.3 |
| M2 | 272 | 16 | trace | trace | 8.0 | 8.3 |
| M3 | 374 | 17.9 | ND | ND | Trace | 3.2 |
| M4 | 418 | 19.2 | ND | ND | Trace | 4.1 |
| M5 | 462 | 20.8 | trace | trace | Trace | 2.3 |
| M6 | 506 | 21.5 | ND | ND | 1 | 2.2 |
| M7 | 550 | 22.3 | trace | trace | 1.2 | 2.2 |
| M8 | 594 | 23 | trace | trace | 1.3 | 2.5 |
| M9 | 638 | 23.6 | trace | trace | Trace | 1.6 |
| M10 | 316 | 16.4 | ND | ND | ND | trace |
| M11 | 360 | 17.9 | ND | ND | Trace | 3.5 |
| M12 | 404 | 19 | ND | ND | trace | 0.7 |
| M13 | 448 | 20.2 | ND | 2.7 | 3.0 | 12.6 |
| M14 | 492 | 21.1 | trace | trace | Trace | 2 |
| M15 | 536 | 21.9 | trace | trace | Trace | 1 |
| M16 | 580 | 22.6 | trace | trace | trace | trace |
| M17 | 624 | 23.2 | trace | trace | trace | trace |
| Others | | | ND | ND | <1.0% | <5.0% |

Example 17

Rat PK

Rat pharmacokinetic ("PK") characterization was conducted in male Sprague Dawley Rats (*Rattus Norvegicus*) weighing between 210-260 gm (Charles River Laboratories (Hollister, Calif.)). Rats were fed a standard diet and water was available ad-libidum at all times. Prior to dosing with metoclopramide and conjugates, rats were fasted overnight and food was returned four hours post dosing. Animals were dosed either orally (2.5 mg/Kg) via gavage or intravenously (0.5 mg/kg) via the jugular vein cannula. Blood samples (~0.15 mL) were collected through carotid artery cannula at respective time points and transferred immediately into K$_2$EDTA-coated tubes (that contain quenching media-acetic acid, PMSF and Dichlorvos) and placed on ice. The samples were centrifuged within thirty minutes after collection at 10,000 RPM for five minutes and the resulting plasma was separated. Plasma were transferred into microfuge tubes and placed on dry ice immediately. The plasma samples were stored at approximately ~70° C. until shipped on dry ice for Bioanalysis by LC/MS/MS. Urine samples were collected using metabolic cages into a tube containing citric acid (4 mg for 0-4 and 4-8 hr interval and 16 mg for 8-24 hr interval) on wet ice at the intervals specified in the study design. After the completion of urine collection at each interval, each cage was rinsed with 2 mL of deionized water (1 mL each time). The rinse was collected in the separate labeled container (containing 2 mg of citric acid) as the urine. Following this rinse another 2 ml rinse was carried out with ethanol (1 ml each time). The rinse was also collected in the separate labeled container as the urine. Samples were stored frozen at −70° C. until bioanalysis by LC/MS/MS was performed.

Pharmacokinetic parameters were determined by non-compartmental analysis using Phoenix®WinNonlin® (Version 6.3; Pharsight Corp., Mountain View, Calif.). Nominal doses and sampling times were used for the analysis. Concentrations reported as BLQ were treated as missing unless they were pre-dose; then they were set to zero. Maximum plasma concentration (Cmax) and time of observed maximum plasma analyte concentration (Tmax) were generated by Phoenix®WinNonlin®, directly from the inputed dataset. Data in the terminal, log-linear phase were analyzed using log-linear regression to estimate the terminal rate constant (k) and the corresponding half-life (t½=0.693/k). Area under the plasma concentration-time curve from time=0 to the time of the last measurable plasma concentration (AUClast) was calculated using linear trapezoidal interpolation until Tmax and log trapezoidal interpolation from Tmax onward. Area under the plasma concentration-time curve from time 0 to infinity (AUCinf) was calculated as the sum of AUClast and the last observed concentration divided by k. Total plasma clearance (CL) was calculated as Dose/AUCinf. Apparent volume of distribution at steady state (Vss) was calculated as MRTinf*CL, where MRT is the mean residence time. Absolute bioavailability after oral administration was calculated using the following equation:

$$\text{Absolute Bioavailability}(\%) = \frac{(AUC_{inf})_{po} * \text{Dose}_{iv}}{(AUC_{inf})_{iv} * \text{Dose}_{po}} * 100.$$

Tables 7 and 8 below gives PK parameters of metoclopramide and conjugates upon IV and oral administration, respectively.

TABLE 7

PK Parameters After Intravenous Administration

| Parameter | Metoclopramide | mPEG$_1$-N-Metoclopramide | mPEG$_4$-N-Metoclopramide | mPEG$_8$-N-Metoclopramide |
|---|---|---|---|---|
| AUC$_{inf}$ [h × ng/mL] | 66.8 | 88.3 | 63.5 | 98.3 |
| CL$_{Tot}$ [mL/min/kg] | 126 | 101 | 133 | 84.4 |
| CL$_{Ren}$ [mL/min/kg] | 7.2* | 4.4 | 9.0 | 0.54 |
| t½ [h] | 0.5 | 0.65 | 0.65 | 2.42 |
| MRT$_{inf}$ [h] | 0.54 | 0.46 | 0.56 | 2.44 |
| V$_{ss}$ [L/kg] | 4.12 | 2.84 | 7.17 | 17.8 |

*From Animal # 5; Animal # 6 had no urine for first 8 hours

TABLE 8

PK Parameters After Oral Administration

| Parameter | Metoclopramide | mPEG$_1$-N-Metoclopramide | mPEG$_4$-N-Metoclopramide | mPEG$_8$-N-Metoclopramide |
|---|---|---|---|---|
| AUC$_{All}$ [h × ng/mL] | 261 | 24.2 | 41.4 | ND |
| CL/F [h × ng/mL] | 131 | 1547 | | NA |
| C$_{max}$ [ng/mL] | 166 | 33.2 | 16.6 | ND |
| C$_{last}$ [ng/mL] | 8.07 | 4.39 | 3 | ND |
| T$_{max}$ [h] | 0.38 | 0.08 | 2 | NA |
| T$_{last}$ [h] | 16 | 2.5 | 5 | NA |
| F [%] | 78 | 6.25 | 14.5 | NA |

Example 18

Metabolism Assays

Metabolic stability of metoclopramide and mPEG$_{3, 5\text{ and }6}$-N-metoclopramide (prepared in accordance with Examples 4, 6 and 7, respectively) was evaluated in human recombinant CYP2D6 enzyme. Final incubation mixture consisted of 1 μM metoclopramide or mPEG$_{3, 5\text{ and }6}$-N-metoclopramide, 1 mM magnesium chloride, 2 mM β-nicotinamide adenine dinucleotide phosphate sodium salt, 20 mM $_D$-glucose 6-phosphate disodium salt hydrate, 0.2 unit/mL of glucose 6-phosphate dehydrogenase, and 100 pmol/mL thawed human recombinant CYP2D6 proteins (Xenotech, LLC) in 100 mM potassium phosphate buffer at pH 7.4. Aliquots of the samples (t=0, 10, 20, and 30 min post incubation in a 70 rpm shaker, 37° C. water bath) were quenched with equal volume of acetonitrile, and metoclopramide and mPEG$_{3, 5\text{ and }6}$-N-metoclopramide were quantified in the supernatants using LC-MS/MS. Results provided in FIG. 5A.

Conclusion: mPEG$_{3, 5\text{ and }6}$-N-Metoclopramide were metabolized by human recombinant CYP2D6 enzyme to a lesser degree than metoclopramide. Each of metoclopramide and mPEG$_{3, 5\text{ and }6}$-N-metoclopramide was chemically stable in 100 mM potassium phosphate buffer, pH 7.4 at 37° C. for up to 30 minutes. Results provided in FIG. 5B.

To assess time-dependent inhibition of CYP2D6, pooled human liver microsomes (Xenotech, LLC) were pre-incubated with metoclopramide and mPEG$_{3, 5\text{ and }6}$-N-metoclopramide (0.1, 0.3, 1, 3, 10, and 30 μM) (prepared in accordance with Examples 4, 6 and 7, respectively) or solvent control and 1 mM NADPH in 100 mM potassium phosphate buffer, pH 7.4 on a 70 rpm shaker in a 37° C. water bath for 1200 sec. The pre-incubation mixture was diluted 10-fold with 1 mM NADPH-containing 100 mM potassium phosphate buffer, 5 μM bufuralol, pH 7.4, and the appearance of 1-hydroxybufuralol, a CYP2D6 specific metabolite of bufuralol, was monitored using LC-MS/MS after incubation for 20 minutes in a 70 rpm shaker, 37° C. water bath followed by protein precipitation with equal volume of acetonitrile. The rate of 1-hydroxybufuralol appearance was compared with that of the solvent control to assess the extent of inhibition of CYP2D6 by each concentration of metoclopramide and mPEG$_{3, 5\text{ and }6}$-N-metoclopramide at a given pre-incubation time point.

Conclusion: The literature reports metoclopramide to be a CYP2D6 time-dependent inhibitor, which suggests that metabolites of metoclopramide inhibit CYP2D6. However, the data from this experimental suggests that neither metoclopramide nor any of mPEG$_{3, 5\text{ and }6}$-N-metoclopramide were found to be time-dependent inhibitors. Assay validity was confirmed by testing in parallel paroxetine, which is a time-dependent inhibitor of CYP2D6. Results provided in FIGS. 6a through 6F.

Figure 7:
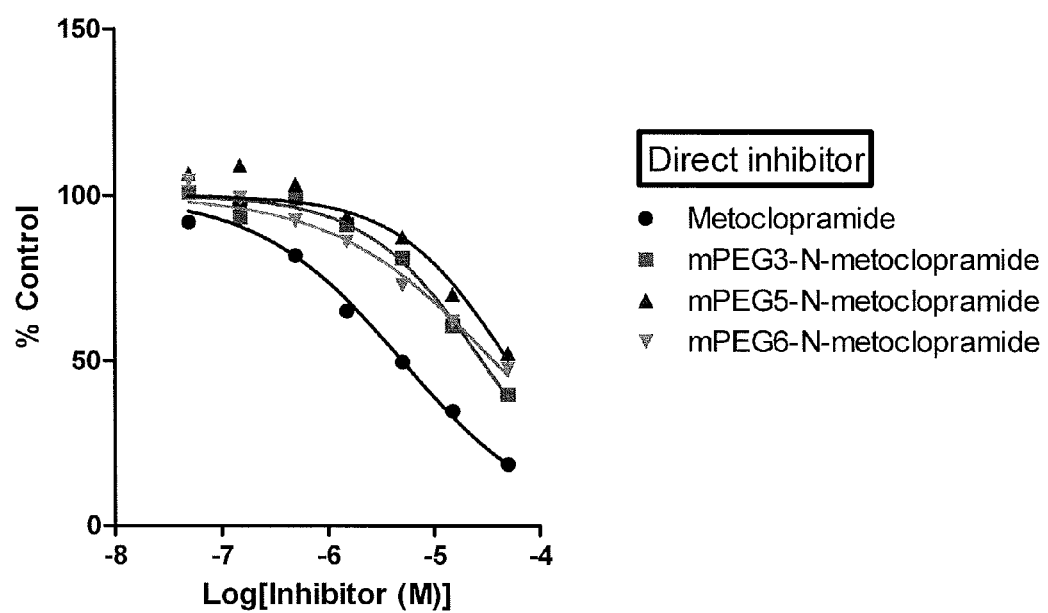
FIG. 7 is a plot representing the extent of inhibition of CYP2D6 by test articles at a series of concentrations, as carried out in the manner described Example 18.

To assess direct inhibition of CYP2D6, metoclopramide, mPEG$_{3, 5\text{ and }6}$-N-metoclopramide (0.05, 0.15, 0.5, 2, 5, 15, 50 μM) (prepared in accordance with Examples 4, 6 and 7, respectively) or the solvent control were incubated with 0.1 mg/mL pooled human liver microsomes, 5 μM bufuralol, and 1 mM magnesium chloride, 2 mM β-nicotinamide adenine dinucleotide phosphate sodium salt, 20 mM $_D$-glucose 6-phosphate disodium salt hydrate, 0.2 unit/mL of glucose 6-phosphate dehydrogenase in 100 mM potassium phosphate buffer at pH 7.4 for 20 minutes in a 70 rpm shaker, 37° C. water bath. At the end of the incubation period, the samples were quenched with equal volume of acetonitrile, and 1-hydroxybufuralol was quantified in the supernatants using LC-MS/MS. The rate of appearance of 1-hydroxybufuralol, a CYP2D6 probe metabolite of bufuralol, was compared with that of the solvent control to assess the extent of direct inhibition of CYP2D6 by each concentration of metoclopramide, mPEG$_{3, 5\text{ and }6}$-N-metoclopramide. Results shown in FIG. 7.

Conclusion: PEG-metoclopramide conjugates showed reduced direct inhibition of CYP2D6-mediated bufuralol metabolism as compared to metoclopramide.

What is claimed is:
1. A compound having the following structure:

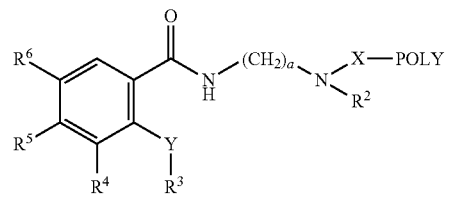

wherein:
R$^2$ is lower alkyl;
(a) is an integer in the range of from 1 to 4 inclusive;
Y is either O or S;
R$^3$ is lower alkyl;
R$^4$ is selected from the group consisting of hydrogen, halo, lower alkoxy, amino, and lower alkylamino;
R$^5$ is selected from the group consisting of hydrogen, halo, lower alkoxy, amino, and lower alkylamino;
R$^6$ is selected from the group consisting of hydrogen, halo, lower alkoxy, amino, and lower alkylamino;

X is a stable or releasable linkage; and

POLY is a water-soluble, non-peptidic oligomer having a number of repeating monomers in the range of from 2 to 30, and pharmaceutically acceptable salts thereof.

2. The compound of claim 1, wherein the linkage is a stable linkage.

3. The compound of claim 1, wherein the linkage is a degradable linkage.

4. The compound of claim 1, wherein the linkage is selected from the group consisting of amine, urea, carbamate and ether.

5. The compound of claim 1, wherein the weight average molecular weight of the water-soluble, non-peptidic oligomer is less than 400 Daltons.

6. The compound of claim 1, having the following structure:

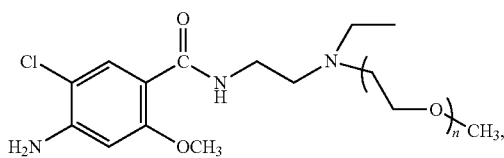

wherein n is in the range of 2 to 30, and pharmaceutically acceptable salts thereof.

7. The compound of claim 1, wherein the water-soluble, non-peptidic oligomer is a poly(alkylene oxide).

8. The compound of claim 7, wherein the poly(alkylene oxide) is a poly(ethylene oxide).

9. The compound of claim 1, wherein the water-soluble, non-peptidic oligomer has a number of repeating monomers in the range of from 2 to 10.

10. The compound of claim 7, wherein the poly(alkylene oxide) includes an alkoxy or hydroxyl end-capping moiety.

11. A composition comprising a compound of claim 1, and (ii) optionally, a pharmaceutically acceptable excipient.

12. A composition of matter comprising a compound of claim 1, wherein the compound is present in a dosage form.

* * * * *